United States Patent
Chen et al.

(10) Patent No.: US 7,202,232 B2
(45) Date of Patent: Apr. 10, 2007

(54) ACRYLONITRILE DERIVATIVES FOR INFLAMMATION AND IMMUNE-RELATED USES

(75) Inventors: Shoujun Chen, Bedford, MA (US); Weiwen Ying, Ayer, MA (US); Jun Jiang, Acton, MA (US); Mitsunori Ono, Lexington, MA (US); Lijun Sun, Harvard, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 11/090,801

(22) Filed: Mar. 24, 2005

(65) Prior Publication Data

US 2005/0272699 A1 Dec. 8, 2005

Related U.S. Application Data

(60) Provisional application No. 60/556,107, filed on Mar. 25, 2004.

(51) Int. Cl.
*A61K 31/724* (2006.01)
*A61K 31/415* (2006.01)
*C07D 231/10* (2006.01)

(52) U.S. Cl. .................. 514/58; 514/406; 548/377.1
(58) Field of Classification Search ............... 514/406; 548/377.1, 365.7; 549/83
See application file for complete search history.

(56) References Cited

U.S. PATENT DOCUMENTS 5,994,355 A * 11/1999 Miki et al. .................. 514/242

OTHER PUBLICATIONS

STN search report for U.S. Patent No. 5,994,355.*

Aviv Gazit, et al. "Tryphostins. 2. Heterocyclic and α-Substituted Benzylidenemalononitrile Tryphostins as Potent Inhibitors of EGF Receptor and ErbB2/neu Tryosine Kinases" J. Med. Chem., 1991, 34, 1896-1907.

Byeong-Kwan An, et al. "Enhanced Emission and Its Switching in Fluorescent Organic Nanoparticles" J. Am. Chem. Soc., 2002, 124, 14410-14415.

Marvin J. Meyers, et al. "Estrogen Receptor-β Potency-Selective Ligands: Structure-Activity Relationship Studies of Diarylpropionitriles and Their Acetylene and Polar Analogues" J. Med. Chem., 2001, 44, 4230-4251.

Yujiro Hayashi, et al. "Disasteroselective Total Synthesis of Both Enantiomers of Epolactaene" J. Org. Chem., 2002, 67, 9443-9448.

Nicolai Stuhr-Hansen, et al. "Novel Synthesis of Protected Thiol End-Capped Stilbenes and Oligo(phenylenevinylene)s (OPVs)" J. Org. Chem., 2003, 68, 1275-1282.

CAPLUS Accession No. 1974:493091, abstract of Kobayashi "3-Phenyl-7-Pyrazolylcoumarin Derivatives", Japanese Patent JP 49000975 (1974), cited p. 1-2.

* cited by examiner

*Primary Examiner*—Kamal A. Saeed
*Assistant Examiner*—Yong Chu
(74) *Attorney, Agent, or Firm*—Jeffrey D. Hsi; Mark D. Russett; Edwards Angell Palmer & Dodge LLP

(57) ABSTRACT

What is claimed is a compound represented by the following structural formula:

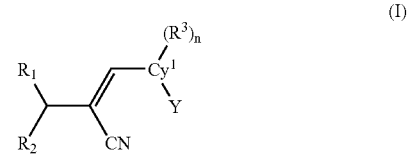

or a pharmaceutically acceptable salt, solvate or clathrate thereof. The variables for Structural Formula (I) are as described herein.

6 Claims, No Drawings

ACRYLONITRILE DERIVATIVES FOR INFLAMMATION AND IMMUNE-RELATED USES

CROSS REFERENCE TO RELATED APPLICATIONS

This application claims the benefit of U.S. Provisional Application No. 60/556,107, filed Mar. 25, 2004, the entire contents of which are incorporated herein by reference.

FIELD OF THE INVENTION

This invention relates to biologically active chemical compounds, namely vinyl cyano derivatives that may be used for immunosuppression or to treat or prevent inflammatory conditions and immune disorders.

BACKGROUND OF THE INVENTION

Interleukin 2 (IL-2) is a T cell-derived lymphokine that modulates immunological effects on many cells of the immune system, including cytotoxic T cells, natural killer cells, activated B cells and lymphokine-activated cells. It is a potent T cell mitogen that is required for the T cell proliferation, promoting their progression from G1 to S phase of the cell cycle. It is a growth factor for all subpopulations of T lymphocytes, as well as stimulating the growth of NK cells. It also acts as a growth factor to B cells and stimulates antibody synthesis.

Due to its effects on both T and B cells, IL-2 is a major central regulator of immune responses. It plays a role in anti-inflammatory reactions, tumour surveillance, and hematopoiesis. It also affects the production of other cytokines, inducing IL-1, TNF-α and TNF-β secretion, as well as stimulating the synthesis of IFN-γ in peripheral leukocytes. IL-2, although useful in the immune response, also causes a variety of problems. IL-2 damages the blood-brain barrier and the endothelium of brain vessels. These effects may be the underlying causes of neuropsychiatric side effects observed under IL-2 therapy, e.g. fatigue, disorientation and depression. It also alters the electrophysiological behaviour of neurons.

T cells that are unable to produce IL-2 become inactive (anergic). This renders them potentially inert to any antigenic stimulation they might receive in the future. As a result, agents which inhibit IL-2 production may be used for immunosupression or to treat or prevent inflammation and immune disorders. This approach has been clinically validated with immunosuppressive drugs such as cyclosporin, FK506, and RS61443. Despite this proof of concept, agents that inhibit IL-2 production remain far from ideal. Among other problems, efficacy limitations and unwanted side effects (including dose-dependant nephrotoxicity and hypertension) hinder their use.

There is therefore a continuing need for new drugs which overcome one or more of the shortcomings of drugs currently used for immunosuppression or in the treatment or prevention of inflammatory disorders and autoimmune disorders. Desirable properties of new drugs include efficacy against diseases or disorders that are currently untreatable or poorly treatable, new mechanism of action, oral bioavailability and/or reduced side effects.

SUMMARY OF THE INVENTION

This invention meets the above-mentioned needs by providing certain acrylonitrile derivatives that inhibit the production of IL-2. These compounds are particularly useful for immunosuppression and/or to treat or prevent inflammatory conditions and immune disorders.

The invention relates to a compound having the formula (I):

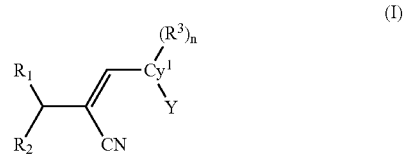

or a pharmaceutically acceptable salt, solvate or clathrate thereof wherein:

$Cy^1$ is a monocyclic or bicyclic aromatic or non-aromatic carbocyclyl or heterocyclyl (preferably aromatic);

Y is a monocyclic or bicyclic, non-aromatic or aromatic carbocyclyl or heterocyclyl;

$R^1$ is =O, =S, =$NOR^4$, or =$C(R^5)(R^5)$;

$R^2$ is a monocyclic or polycyclic, non-aromatic or aromatic carbocyclyl or heterocyclyl, wherein when $R^1$ is =O, then $R^2$ is phenyl substituted with one or more halogen, lower perfluoroalkyl or lower perfluoroalkoxy; or $R^1$ and $R^2$ taken together may form a monocyclic or polycyclic, non-aromatic or aromatic carbocyclyl or heterocyclyl;

each $R^3$ is a substituent bonded to $Cy^1$ and is independently selected from halogen, lower alkyl, lower haloalkyl, lower alkoxy, lower haloalkoxy, CN, $NO_2$, $OR^4$, $N(R^4)(R^4)$, $SR^4$, $CO_2R^4$, $CON(R^4)(R^4)$, $SOR^6$, $SO_2R^6$, $COR^4$, $NR^4COR^4$, $NR^4CON(R^4)(R^4)$, $SO_2N(R^4)(R^4)$, $NR^4SOR^6$, and $Ar^2$.

n is an integer selected from 0, 1, 2 or 3;

each $Ar^2$ is independently aryl or heteroaryl optionally substituted with halogen, lower alkyl, lower haloalkyl (preferably lower perfluoroalkyl), lower alkoxy, lower haloalkoxy (preferably lower perfluoroalkoxy), CN, $NO_2$, $R^6$, $OR^4$, $N(R^4)(R^4)$, $SR^4$, $CO_2R^4$, $CON(R^4)(R^4)$, $SOR^6$, $SO_2R^6$, $COR^4$, $NR^4COR^4$, $NR^4CON(R^4)(R^4)$, $SO_2N(R^4)(R^4)$, or $NR^4SOR^6$;

each $R^4$ is independently hydrogen or alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio;

each $R^5$ is independently CN or $CO_2R^4$; and each $R^6$ is independently alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio.

The invention further encompasses methods for inhibiting IL-2 production in vivo or in vitro using an effective amount of a disclosed compound or a pharmaceutically acceptable salt, solvate or clathrate thereof or a pharmaceutical composition comprising an effective amount of a compound disclosed herein. All of the methods of this invention may be practiced using a compound disclosed herein alone or in combination with other agents, such as other immunosuppressive, anti-inflammatory or immune disorder agents.

DETAILED DESCRIPTION OF THE INVENTION

Definitions

Unless otherwise specified, the below terms used herein are defined as follows:

As used herein, the term "aromatic ring", "aryl" (either alone or as part of another term, e.g., alkylaryl, aryloxy, arylamino and the like) means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more conventional aryl substituents (including without limitation alkyl (preferably, lower alkyl or alkyl substituted with one or more halo), hydroxy, alkoxy (preferably, lower alkoxy), alkylthio, cyano, halo, amino, and nitro. Preferably, the aryl group is a monocyclic ring, wherein the ring comprises 6 carbon atoms.

As used herein, the term "carbocyclyl" (either alone or as part of another term, e.g., carbocyclyloxy, carbocyclylthio, carbocyclylamino and the like) means a monocyclic or polycyclic aromatic or non-aromatic ring or ring radical comprising carbon and hydrogen atoms. Examples of suitable carbocyclyl groups include, but are not limited to, phenyl, tolyl, anthacenyl, fluorenyl, indenyl, azulenyl, naphthyl, benzo-fused carbocyclic moieties such as 5,6,7,8-tetrahydronaphthyl, cycloalkyl, cycloalkenyl, bicycloalkyl and bicycloalkenyl groups. A carbocyclyl group can be unsubstituted or substituted with one or more conventional aryl substituents (including without limitation alkyl (preferably, lower alkyl or alkyl substituted with one or more halo), hydroxy, alkoxy (preferably, lower alkoxy), alkylthio, cyano, halo, amino, and nitro. Preferably, the carbocyclyl group is a monocyclic ring, wherein the ring comprises 6 carbon atoms.

As used herein, the term "alkyl" (either alone or as part of another term, e.g., alkylaryl, alkylamino, alkylthio, alkoxy and the like) means a saturated straight chain or branched non-cyclic hydrocarbon typically having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, -2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more conventionally used alkyl substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocylythio, and the like. In addition, a carbon in the alkyl segment, typically an internal carbon atom in an alkyl segment, may be substituted with carbonyl (C=O), thiocarbonyl (C=S), oxygen (O), sulfur (S), or nitrogen (N). Lower alkyls are typically preferred for the compounds of this invention.

As used herein, the term "alkenyl" (either alone or as part of another term) means an alkyl radical typically having from 2 to 10 carbon atoms and having at least one carbon-carbon double bond. Representative straight chain and branched alkenyls include -vinyl, -allyl, -1-butenyl, -2-butenyl, -isobutylenyl, -1-pentenyl, -2-pentenyl, -3-methyl-1-butenyl, -2-methyl-2-butenyl, 2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

As used herein, the term "alkynyl" (either alone or as part of another term) means an alkyl radical typically having from 2 to 10 carbon atoms and having at lease one carbon-carbon triple bond. Representative straight chain and branched alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

As used herein, the term "cycloalkyl" (either alone or as part of another term) means a saturated cyclic alkyl radical typically having from 3 to 10 carbon atoms. Representative cycloalkyls include -cyclopropyl, -cyclobutyl, -cyclopentyl, -cyclohexyl, -cycloheptyl, -cyclooctyl, -cyclononyl, and -cyclodecyl.

As used herein, the term "bicycloalkyl" (either alone or as part of another term) means a bi-cyclic alkyl system typically having from 8 to 14 carbon atoms and at least one saturated cyclic alkyl ring. Representative bicyclocycloalkyls include -indanyl, -1,2,3,4-tetrahydronaphthyl, -5,6,7,8-tetrahydronaphthyl, -perhydronaphthyl and the like.

As used herein, the term "cycloalkenyl" (either alone or as part of another term) means a cyclic non-aromatic alkyl radical having at least one carbon-carbon double bond in the cyclic system and typically having from 5 to 10 carbon atoms. Representative cycloalkenyls include -cyclopentenyl, -cyclopentadienyl, -cyclohexenyl, -cyclohexadienyl,-cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

As used herein, the term "heterocycle" or "heterocyclyl" (either alone or as part of another term) means a monocyclic or bicyclic heterocyclic ring (typically having 3- to 10-members) which is either saturated, unsaturated non-aromatic, or aromatic. A 3-membered heterocycle can contain up to 3 heteroatoms, and a 4- to 10-membered heterocycle can contain up to 4 heteroatoms. Each heteroatom is independently selected from nitrogen, which can be quaternized; oxygen; and sulfur, including sulfoxide and sulfone. The heterocycle may be attached via a heteroatom or carbon atom. Representative heterocycles include pyridyl, furyl, thiophenyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, morpholinyl, pyrrolidinonyl, pyrrolidinyl, piperidinyl, piperazinyl, benzo[1,3] dioxolyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. Benzo-fused saturated heterocycles, such 1,2,3,4-tetrahydroquinoline are expressly included in this definition. A heteroatom may be substituted with a protecting group known to those of ordinary skill in the art, for example, the hydrogen on a nitrogen may be substituted with a tert-butoxycarbonyl group. Furthermore, the heterocyclic ring may be optionally substituted with one or more conventional heterocyclic ring substituents (including without limitation a halogen atom, an alkyl radical, or aryl radical). Only stable isomers of such substituted heterocyclic groups are contemplated in this definition.

As used herein, the term "heteroaromatic", "heteroaryl" (either alone or as part of another term) means a monocyclic or polycyclic heteroaromatic ring (or radical thereof) comprising carbon atom ring members and one or more heteroatom ring members (such as, for example, oxygen, sulfur or nitrogen). In one embodiment, the heteroaromatic ring is selected from 5–8 membered heteroaryl rings. In another embodiment, the heteroaromatic ring is a 5 or 6 membered ring. Representative heteroaryls include furyl, thienyl, pyrrolyl, oxazolyl, imidazolyl, indolizinyl, thiazolyl, isoxazolyl, pyrazolyl, isothiazolyl, pyridinyl, pyridazinlyl, pyrazinlyl, triazolyl, thiadiazolyl, benzofuryl, benzothienyl, indolyl, isoindolyl, benzoxazolyl, benzimidazolyl, benzothiazolyl, isoxazolyl, indazolyl, benzoisothiazolyl, benzopyrazinyl, benzotriazolyl, benzothiadiazolyl, quinolyl, isoquinolyl, quinazolyl, phthalazolyl, cinnolyl, and the like. These heteroaryl groups (including indolizinyl when mentioned alone) may be optionally substituted with one or more known heteroaryl substituents including (but not limited to amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like. Particular heteroaryl substituents include halo and lower alkyl optionally substituted with one or more halo.

As used herein, the term "halogen", "halo" (either alone or as part of another term) means —F, —Cl, —Br or —I.

As used herein, the terms "subject", "patient", and "animal", are used interchangeably and include, but are not limited to, a cow, monkey, horse, sheep, pig, birds (such as chicken, turkey, quail, and the like), cat, dog, mouse, rat, rabbit, guinea pig and human. These terms include mammals and non-mammals. The preferred subject, patient or animal is a mammal, preferably a human.

As used herein, the term "lower" refers to a group having up to four atoms. For example, a "lower alkyl" refers to an alkyl radical having from 1 to 4 carbon atoms, and a "lower alkenyl" or "lower alkynyl" refers to an alkenyl or alkynyl radical having from 2 to 4 carbon atoms, respectively. Lower substituents are typically preferred.

Where a particular substituent occurs multiple times in a given structure or moeity, the identity of the substituent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

As used herein, the term "pharmaceutically acceptable salt," is a salt formed from an acid and a basic group of one of the disclosed compounds. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, ρ-toluenesulfonate, and pamoate (i.e., 1,1'-methylene-bis-(2-hydroxy-3-naphthoate)) salts. The term "pharmaceutically acceptable salt" also refers to a salt prepared from a disclosed compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

As used herein, the term "pharmaceutically acceptable solvate," is a solvate formed from the association of one or more solvent molecules to one of the disclosed compounds. The term solvate includes hydrates (e.g., mono-hydrate, dihydrate, trihydrate, tetrahydrate, and the like).

As used herein, the term "asthma" means a pulmonary disease, disorder or condition characterized by reversible airway obstruction, airway inflammation, and increased airway responsiveness to a variety of stimuli.

"Immunosuppression" refers to impairment of a component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200–210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415–1450, Taylor & Francis, Philadelphia, Pa.).

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the brain in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

The compounds of this invention can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection, such as skin graft rejection or rejection of transplanted islet of Langerhans in a diabetic subject; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

Compounds of the invention may also be used to treat a subject in need of immunosuppression, such as a subject that has undergone a skin graft or organ transplant (e.g., a diabetic subject that has undergone transplantation of islets of Langerhans).

An "effective amount" is the quantity of compound in which a beneficial outcome is achieved when the compound is administered to a subject or alternatively, the quantity of compound that possess a desired activity in vivo or in vitro. In the case of inflammatory disorders and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder or autoimmune disorder or the degree of immunosuppression sought. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 1 gram/mm$^2$.

The compounds of the invention may contain one or more chiral centers and/or double bonds and, therefore, exist as stereoisomers, such as double-bond isomers (i.e., geometric isomers), enantiomers, or diastereomers. With respect to the compounds depicted herein by structure or by name, unless the stereochemistry at a particular atom is defined, it is understood that all of the corresponding compounds' enantiomers and stereoisomers, that is, both the stereomerically pure form (e.g., geometrically pure, enantiomerically pure, or diastereomerically pure) and enantiomeric and stereoisomeric mixtures.

The term "inhibit production of IL-2" and like terms means inhibiting IL-2 synthesis (e.g. by inhibiting transcription (mRNA expression), or translation (protein expression)) and/or inhibiting IL-2 secretion in a cell that has the ability to produce and/or secrete IL-2 (e.g., T lymphocyte).

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the disclosed compounds.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

Specific Embodiments

The invention relates to compounds and pharmaceutical compositions that are particularly useful for immunosuppression or to treat or prevent inflammatory conditions and immune disorders.

Specific methods and pharmaceutical compositions of the invention comprise a disclosed compound as an active ingredient.

One embodiment of the invention relates to methods for immunosuppression or for treating or preventing inflammatory conditions or immune disorders in a patient in need thereof comprising administering an effective amount of a compound disclosed herein.

One embodiment of the present invention is a compound represented by structural formula (I):

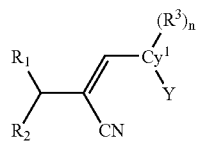

(I)

or a pharmaceutically acceptable salt, solvate or clathrate thereof wherein:
$Cy^1$ is a monocyclic or bicyclic aromatic or non-aromatic carbocyclyl or heterocyclyl (preferably aromatic);
Y is a monocyclic or bicyclic, non-aromatic or aromatic carbocyclyl or heterocyclyl;
$R^1$ is =O, =S, =NOR$^4$, or =C(R$^5$)(R$^5$);
$R^2$ is a monocyclic or polycyclic, non-aromatic or aromatic carbocyclyl or heterocyclyl, wherein when $R^1$ is =O, then $R^2$ is phenyl substituted with one or more halogen, lower perfluoroalkyl or lower perfluoroalkoxy; or $R^1$ and $R^2$ taken together may form a monocyclic or polycyclic, non-aromatic or aromatic carbocyclyl or heterocyclyl;
each $R^3$ is a substituent bonded to $Cy^1$ and is independently selected from halogen, lower alkyl, lower haloalkyl, lower alkoxy, lower haloalkoxy, CN, NO$_2$, OR$^4$, N(R$^4$)(R$^4$), SR$^4$, CO$_2$R$^4$, CON(R$^4$)(R$^4$), SOR$^6$, SO$_2$R$^6$, COR$^4$, NR$^4$COR$^4$, NR$^4$CON(R$^4$)(R$^4$), SO$_2$N(R$^4$)(R$^4$), NR$^4$SOR$^6$, and Ar$^2$.
n is an integer selected from 0, 1, 2 or 3;
each Ar$^2$ is independently aryl or heteroaryl optionally substituted with halogen, lower alkyl, lower haloalkyl (preferably lower perfluoroalkyl), lower alkoxy, lower haloalkoxy (preferably perfluoroalkoxy), CN, NO$_2$, R$^6$, OR$^4$, N(R$^4$)(R$^4$), SR$^4$, CO$_2$R$^4$, CON(R$^4$)(R$^4$), SOR$^6$, SO$_2$R$^6$, COR$^4$, NR$^4$COR$^4$, NR$^4$CON(R$^4$)(R$^4$), SO$_2$N(R$^4$)(R$^4$), or NR$^4$SOR$^6$;
each $R^4$ is independently hydrogen or alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio;
each $R^5$ is independently CN or CO$_2$R$^4$; and
each $R^6$ is independently alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio.

Another embodiment of the present invention is a compound represented by Structural Formula (I) wherein:
$Cy^1$ is phenyl, pyridinyl, pyridazinyl, pyrazinyl, pyrimidinyl, tetrazolyl, furyl, thienyl, pyrrolyl, oxazolyl, imidazolyl, thiazolyl, isoxazolyl, pyrazolyl, isothiazolyl, oxadiazolyl, triazolyl, or thiadiazolyl optionally fused with benzene, pyridine, pyrimidine, triazine, tetrazine, furan, thiophene, pyrrole, oxazole, imidazole, thiazole, isoxazole, pyrazole, or isothiazole; and the remainder of the variables in Structural Formula (I) are as described above.

Another embodiment of the present invention is a compound represented by Structural Formula (I), wherein:

$Cy^1$ is a radical of formula (II), (III), (IV), (V) (VI), (VII), (VIII), (X), (XI), or (XII):

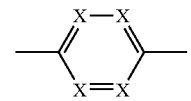

(II)

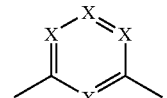

(III)

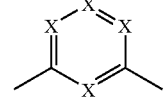

(IV)

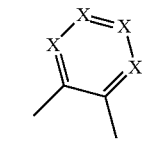

(V)

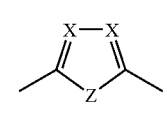

(VI)

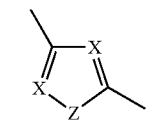

(VII)

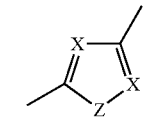

(VIII)

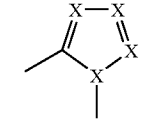

(IX)

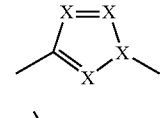

(X)

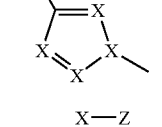

(XI)

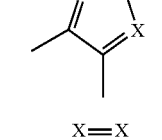

(XII)

each formulae (I) to (XII) is optionally fused with benzene, pyridine, pyrimidine, triazine, tetrazine, furan, thiophene, pyrrole, oxazole, imidazole, thiazole, isoxazole, pyrazole, or isothiazole.
Z is O, S or NR$^4$.
each X is independently CH, CR$^3$ or N.
The remainder of the variables are as described above.

Another embodiment of the present invention is a compound represented by Structural Formula (XIII):

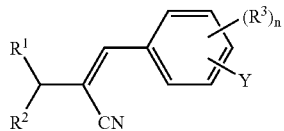

(XIII)

or a pharmaceutically acceptable salt, solvate or clathrate thereof wherein:
$R^1$ is =O, =S, =NOR$^4$, or =C(R$^5$)$_2$ and $R^2$ is aryl, cycloalkyl, bicycloalkyl, cycloalkenyl, bicycloalkyenyl or hetercyclyl, wherein when $R^1$ is =O, then $R^2$ is phenyl substituted with one or more halogen, lower perfluoroalkyl or lower perfluoroalkoxy or $R^1$ and $R^2$ taken together form aryl, cycloalkyl, bicycloalkyl, cycloalkenyl, bicycloalkyenyl or hetercyclyl;
preferably, $R^1$ and $R^2$ taken together form aryl, cycloalkyl, bicycloalkyl, cycloalkenyl, bicycloalkyenyl or hetercycly;
more preferably, $R^1$ and $R^2$ taken together form an optionally substituted phenyl, more preferably 1, 4-phenyl substituted with one or more halogen, perfluoroalkyl or perfluoroalkoxy.

The remainder of the variables in Structural Formula (XIII) are as described for Structural Formula (I) above.

Another embodiment is a compound represented by Structural Formula (XIII) wherein $R^2$ is C=O and the remainder of the variables are as described above.

Another embodiment of the present invention is a compound represented by Structural Formula (XIV):

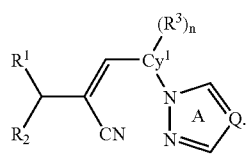

(XIV)

or a pharmaceutically acceptable salt, solvate or clathrate thereof.
Q is CH or N, preferably CH.
Ring A is optionally substituted at any substitutable carbon atom and is optionally fused to an optionally substituted phenyl ring.
$R^1$ is =O, =S, =NOR$^4$, or =C(R$^5$)(R$^5$).
$R^2$ is a monocyclic or polycyclic, non-aromatic or aromatic carbocyclyl or heterocyclyl; or $R^1$ and $R^2$ taken together may form a monocyclic or polycyclic, non-aromatic or aromatic carbocyclyl or heterocyclyl. Preferably when $R^1$ is =O, then $R^2$ is phenyl substituted with one or more halogen, lower perfluoroalkyl or lower perfluoroalkoxy.

The remainder of the variables in Structural Formula (XIV) are as described for Structural Formula (I).

Another embodiment of the present invention is a compound represented by Structural Formula (XIV) wherein:
Cy$^1$ is phenyl, pyridinyl, pyridazinyl, pyrazinyl, pyrimidinyl, tetrazolyl, furyl, thienyl, pyrrolyl, oxazolyl, imidazolyl, thiazolyl, isoxazolyl, pyrazolyl, isothiazolyl, oxadiazolyl, triazolyl, or thiadiazolyl optionally fused with benzene, pyridine, pyrimidine, triazine, tetrazine, furan, thiophene, pyrrole, oxazole, imidazole, thiazole, isoxazole, pyrazole, or isothiazole; and the remainder of the variables in Structural Formula (XIV) are as described above.

Another embodiment of the present invention is a compound represented by Structural Formula (XIV), wherein:
Cy$^1$ is a radical of formula (II), (III), (IV), (V) (VI), (VII), (VIII), (X), (XI), or (XII). The remainder of the variables in Structural Formula (XIV) are as described above.

Another embodiment of the present invention is a compound represented by Structural Formulas (XV) or (XVI):

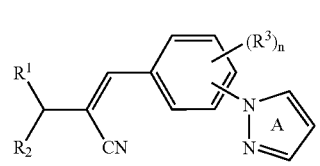

(XV)

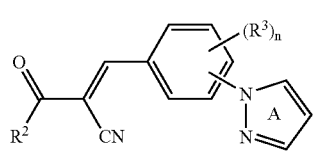

(XVI)

The variables in Structural Formulas (XV) and (XVI) are as described above for Structural Formula (XIV). Preferably, in Structural Formula (XV), $R^1$ and $R^2$ taken together are an optionally substituted aryl (preferably phenyl); and in Structural Formula (XVI), $R^2$ is an optionally substituted phenyl. More preferably, Ring A and the aryl group (preferably phenyl ring) formed from $R^1$ and $R^2$ (in Structural Formula (XV)) and the aryl group (preferably phenyl ring) represented by $R^2$ (in Structural Formula (XVI)) are optionally and independently substituted with one or more groups independently selected from halogen, lower alkyl, lower haloalkyl (preferably lower perfluoroalkyl), lower alkoxy, lower haloalkoxy (preferably lower perfluoroalkoxy), CN, NO$_2$, R$^6$, OR$^4$, N(R$^4$)(R$^4$), SR$^4$, CO$_2$R$^4$, CON(R$^4$)(R$^4$), SOR$^6$, SO$_2$R$^6$, COR$^4$, NR$^4$COR$^4$, NR$^4$CON(R$^4$)(R$^4$), SO$_2$N(R$^4$)(R$^4$), and NR$^4$SOR$^6$.

Even more preferably, the compound of the present invention is represented by Structural Formulas (XVII) or (XVIII):

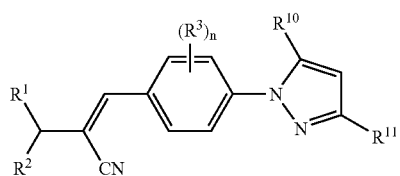

(XVII)

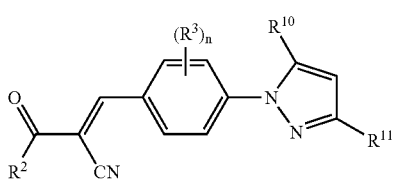

(XVIII)

$R^{10}$ and $R^{11}$ are independently —H, lower alkyl, lower haloalkyl, furanyl, thienyl, phenyl, lower alkoxy or lower haloalkoxy and each $R^3$ is independently —H, lower alkyl, lower haloalkyl, lower alkoxy or lower haloalkoxy. The remainder of the variables in Structural Formulas (XVII) and (XVIII) are as described above for Structural Formulas (XV) and (XVI). More preferably, $R^3$ is independently —H, lower alkyl, lower haloalkyl, lower alkoxy or lower haloalkoxy; the aryl group (preferably phenyl ring) formed from $R^1$ and $R^2$ (in Structural Formula (XVII)) and the aryl group (preferably phenyl ring) represented by $R^2$ (in Structural Formula (XVIII)) are substituted with one or more halogens, lower perfluoroalkyl or lower perfluoroalkoxy; and $R^{10}$ and $R^{11}$ are independently —H, lower alkyl, or lower perfluoroalkyl.

Another embodiment of the invention encompasses a pharmaceutical composition comprising an effective amount of a compound disclosed herein or a pharmaceutically acceptable salt, solvate or clathrate thereof. The compositions are useful for immunosuppression or to treat or prevent inflammatory conditions and immune disorders.

A further embodiment of the invention encompasses a method of suppressing the immune system in a subject in need thereof, which comprises administering to the subject an effective amount of a compound disclosed herein or a pharmaceutically acceptable salt, solvate or clathrate thereof, or a pharmaceutical composition comprising a compound disclosed herein or a pharmaceutically acceptable salt, solvate or clathrate thereof. In general, a physician or veterinarian can determine whether a subject is in need of immunosuppression. Typically, a subject who has undergone organ transplantation will be in need of immunosuppression. In another embodiment, a subject who has an autoimmune disorder or inflammatory condition may be in need of immunosuppression.

A further embodiment of the invention encompasses a method of immunosuppression or for treating or preventing inflammatory conditions and immune disorders, which comprises administering to a patient in need thereof an effective amount of a compound disclosed herein or a pharmaceutically acceptable salt, solvate or clathrate thereof, or a pharmaceutical composition comprising a compound disclosed herein or a pharmaceutically acceptable salt, solvate or clathrate thereof.

Yet another embodiment of the invention encompasses a method of inhibiting IL-2 production using an effective amount of a compound disclosed herein or a pharmaceutically acceptable salt, solvate or clathrate thereof, or pharmaceutical composition comprising a compound disclosed herein or a pharmaceutically acceptable salt, solvate or clathrate thereof.

The substituents used for compounds of formula (I) or any of the specific compound shown below can be used in any combination that results in the formation of a stable compound. All such combinations are expressly encompassed in this invention.

Exemplary compounds of the invention are depicted in the Table shown in Example 2.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Methods of Treatment and Prevention

In accordance with the invention, an effective amount of a compound disclosed herein or a pharmaceutically acceptable salt, solvate or clathrate thereof, or a pharmaceutical composition comprising a compound disclosed herein or a pharmaceutically acceptable salt, solvate or clathrate thereof, is administered to a patient in need of immunosuppression or in need of treatment or prevention of an inflammatory condition or immune disorder.

Responsiveness of a particular inflammatory condition or immune disorder in a subject can be measured directly (e.g., measuring blood levels of inflammatory cytokines (such as IL-2, IFN-γ and the like) after administration of a compound or formulation of this invention), or can be inferred based on an understanding of disease etiology and progression. The disclosed compounds or pharmaceutically acceptable salts, solvates or clathrates thereof can be assayed in vitro or in vivo, for the desired therapeutic or prophylactic activity, prior to use in humans. For example, known animal models of inflammatory conditions or immune disorders can be used to demonstrate the safety and efficacy of compounds of this invention.

Pharmaceutical Compositions and Dosage Forms

Pharmaceutical compositions and dosage forms of the invention comprise one or more active ingredients in relative amounts and formulated in such a way that a given pharmaceutical composition or dosage form can be used for immunosuppression or to treat or prevent inflammatory conditions and immune disorders. Preferred pharmaceutical compositions and dosage forms comprise a disclosed compound or a pharmaceutically acceptable salt, solvate, or clathrate thereof, optionally in combination with one or more additional active agents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379–80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a disclosed compound or a pharmaceutically acceptable salt, solvate or clathrate thereof in an amount of from about 1 mg to about 1000 mg, preferably in an amount of from about 50 mg to about 500 mg, and most preferably in an amount of from about 75 mg to about 350 mg. The typical total daily dosage of a disclosed compound or a pharmaceutically acceptable salt, solvate or clathrate thereof can range from about 1 mg to about 5000 mg per day, preferably in an amount from about 50 mg to about 1500 mg per day, more preferably from about 75 mg to about 1000 mg per day. It is within the skill of the art to determine the appropriate dose and dosage form for a given patient.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a disclosed compound, or a pharmaceutically acceptable salt, solvate, hydrate or clathrate thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entirely of which is incorporated herein by reference.

A specific controlled-release formulation of this invention comprises from about 6% to about 40% a disclosed compound by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

Parenteral Dosage forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which-a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Combination Therapy

The methods for immunosuppression or for treating or preventing inflammatory conditions and immune disorders in a patient in need thereof can further comprise administering to the patient being administered a compound of this invention, an effective amount of one or more other active agents. Such active agents may include those used conventionally for immunosuppression or for inflammatory conditions or immune disorders. These other active agents may also be those that provide other benefits when administered in combination with the compounds of this invention. For example, other therapeutic agents may include, without limitation, steroids, non-steroidal anti-inflammatory agents, antihistamines, analgesics, immunosuppressive agents and suitable mixtures thereof. In such combination therapy treatment, both the compounds of this invention and the other drug agent(s) are administered to a subject (e.g., humans, male or female) by conventional methods. The agents may be administered in a single dosage form or in separate dosage forms. Effective amounts of the other therapeutic agents and dosage forms are well known to those skilled in the art. It is well within the skilled artisan's purview to determine the other therapeutic agent's optimal effective-amount range.

In one embodiment of the invention where another therapeutic agent is administered to a subject, the effective amount of the compound of this invention is less than its effective amount when the other therapeutic agent is not administered. In another embodiment, the effective amount of the conventional agent is less than its effective amount when the compound of this invention is not administered. In this way, undesired side effects associated with high doses of either agent may be minimized. Other potential advantages (including without limitation improved dosing regimens and/or reduced drug cost) will be apparent to those of skill in the art.

In one embodiment relating to autoimmune and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see *Paul A. Insel, Analgesic-Antipyretic and Antiinflammatory Agents and Drugs Employed in the Treatment of Gout*, in *Goodman & Gilman's The Pharmacological Basis of Therapeutics* 617–57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy Vol II* 1196–1221 (A. R. Gennaro ed. 19th ed. 1995) which are hereby incorporated by reference in their entireties. Of particular relevance to allergic disorders, the other therapeutic agent may be an anthihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of anthihistamines, see *Goodman & Gilman's The Pharmacological Basis of Therapeutics* (2001) 651–57, $10^{th}$ ed).

Immunosuppressive agents include glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, buslfan, and cyclophosphamide), folic acid antagonsists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

The foregoing and other useful combination therapies will be understood and appreciated by those of skill in the art. Potential advantages of such combination therapies include a different efficacy profile, the ability to use less of each of the individual active ingredients to minimize toxic side effects, synergistic improvements in efficacy, improved ease of administration or use and/or reduced overall expense of compound preparation or formulation.

Other Embodiments

The compounds of this invention may be used as research tools (for example, as a positive control for evaluating other IL-2 inhibitors. These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

The contents of all references, including patents and patent applications, cited throughout this specification are hereby incorporated herein by reference in their entirety.

EXAMPLES

Materials and General Methods

Reagents and solvents used below can be obtained from commercial sources such as Aldrich Chemical Co. (Milwaukee, Wis., USA). 1H-NMR and 13C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

General Synthetic Methods

The preparation of the compounds of the present invention is shown schematically in Schemes 1–5 below. Detailed experimental procedures for individual compounds are provided in the Exemplification Section. Compounds of the invention not specifically exemplified can be prepared by suitable selection of the starting materials and routine variation of the experimental conditions.

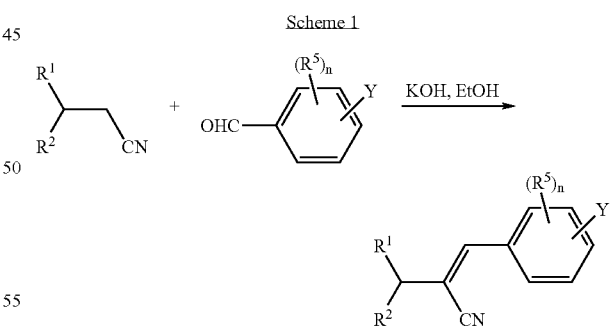

Scheme 1

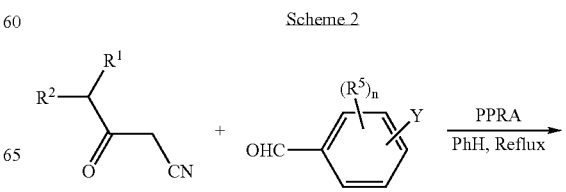

Scheme 2

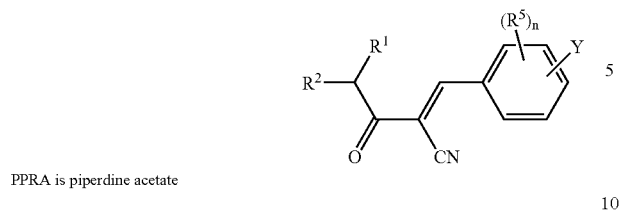
PPRA is piperdine acetate
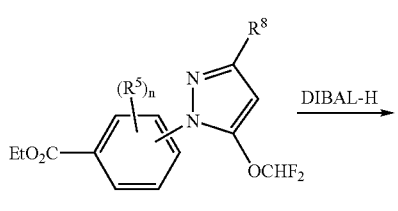
Scheme 3
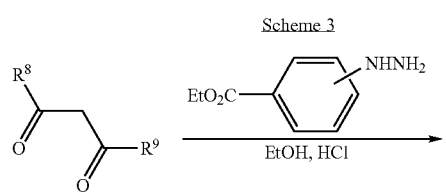
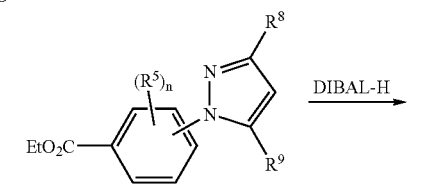
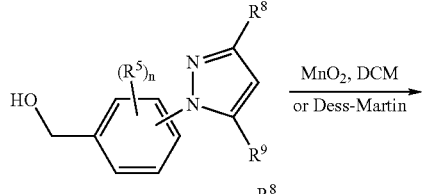
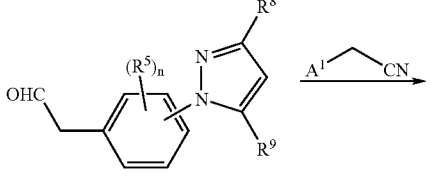
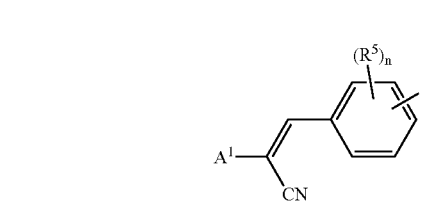
Scheme 4
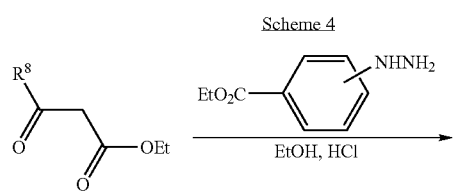
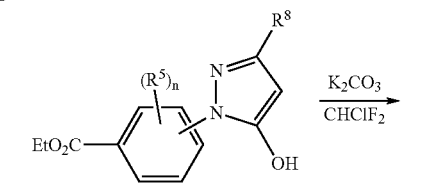
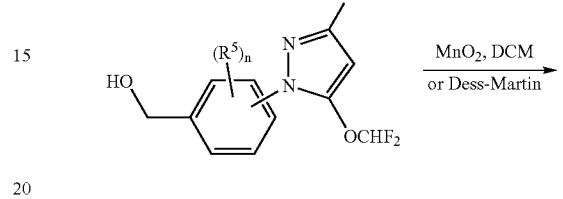
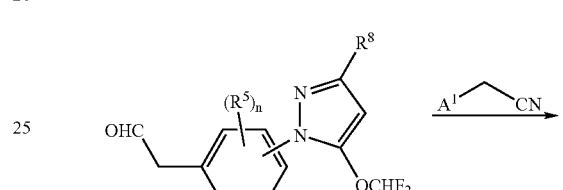
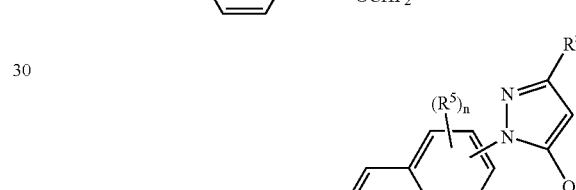
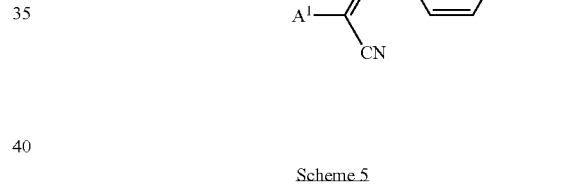
Scheme 5
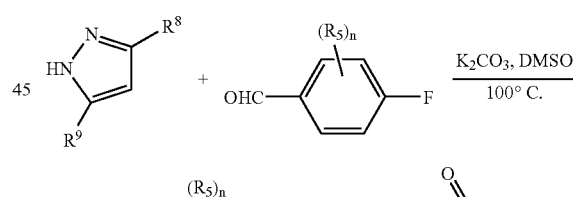
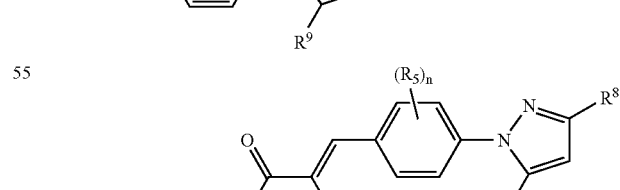
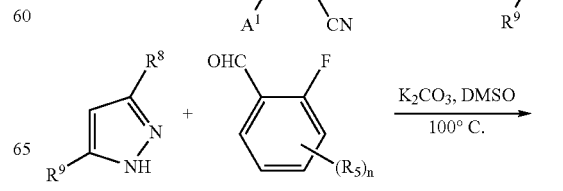

-continued

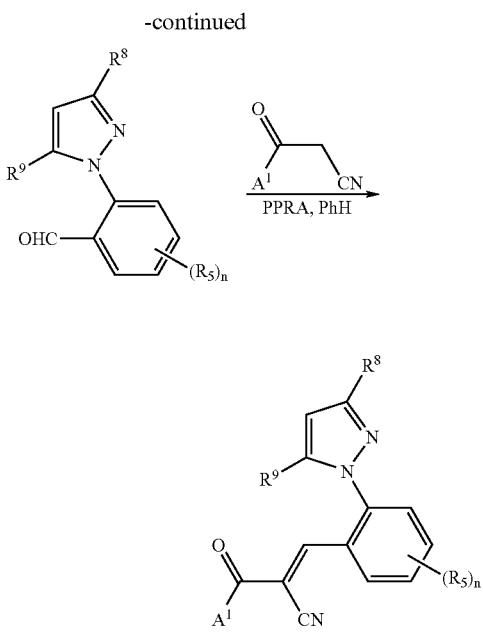

PPRA is piperdine acetate

Exemplification

Example 1

Synthesis of Representative Exemplary Compounds of this Invention

Compound 1: 5-Difluoromethoxy-1-{4-[2-(2,3-difluoro-phenyl)-2-isocyano-vinyl]-phenyl}-3-trifluoromethyl-1H-pyrazole

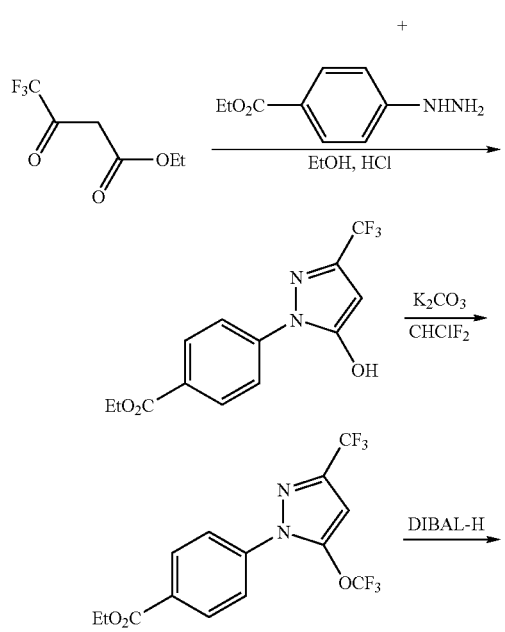

-continued

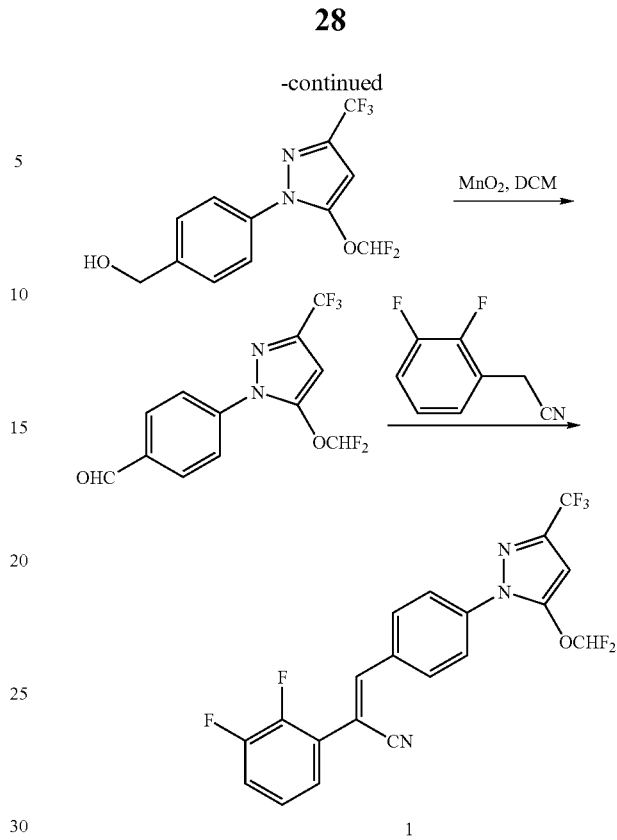

Step 1: A mixture of trfluoroacetoacetic acid ethyl ester (3.68 g, 20 mmol) and 4-hydrazinobenzoic acid hydrochloride (3.77 g, 20 mmol) in ethanol (15 mL) was stirred at 100° C. in a sealed tube for 8 hours. The mixture was cooled to room temperature and the solvent was removed under reduced pressure. The residue was triturated with ether/hexane (5:1 v/v) to provide 4-(5-hydroxy-3-trifluoromethyl-pyrazol-1-yl)-benzoic acid ethyl ester (2.67 g, 45% yield) as an off white solid.

Step 2: A mixture of 4-(5-hydroxy-3-trifluoromethyl-pyrazol-1-yl)-benzoic acid ethyl ester (1 g, 3.3 mmol), difluorochloromethane (3 g, 34 mmol) and potassium carbonate (0.5 g, 3.6 mmol) in DMF (9 mL) was stirred in a sealed tube at −78° C. for 3 minutes and then at 100° C. for 12 hours. The mixture was cooled to −78° C. and the precipitate was removed by filtration and washed with DMF (3×1 mL). The filtrate and washings were poured into cold water (200 mL). The resulting suspension was transferred into a centrifuge tube and the contents were centrifuged at room temperature for 10 minutes and filtered to give 4-(5-difluoromethoxy-3-trifluoromethyl-pyrazol-1-yl)-benzoic acid ethyl ester (1.1 g, 94% yield) as a yellow solid.

Step 3: A solution of 4-(5-difluoromethoxy-3-trifluoromethyl-pyrazol-1-yl)-benzoic acid ethyl ester (0.4 g, 1.1 mmol) in dry toluene (8.0 mL) was stirred and 1M solution of DIBAL-H in toluene (1.33 mL, 1.33 mmol) was added. The resultant solution was stirred at room temperature for 10 minutes. The mixture was quenched with saturated aqueous $NH_4Cl$ (40 mL) and extracted with EtOAc (3×40 mL). The organics were washed with water and brine. The solvent was removed under reduced pressure and purification of the resulting residue by chromatography ($SiO_2$, 10:1 Hexane/

EtOAc) gave [4-(5-difluoromethoxy-3-trifluoromethyl-pyrazol-1-yl)-phenyl]-methanol (380 mg, 99% yield) as a syrup.

Step 4: A solution of [4-(5-difluoromethoxy-3-trifluoromethyl-pyrazol-1-yl)-phenyl]-methanol (380 mg, 1.2 mmol) in DCM (20 mL) was treated with excess amount of $MnO_2$ was stirred at room temperature for 24 hours. The mixture was filtered and the filtrate was concentrated under reduced pressure. Purification by chromatography ($SiO_2$, 6:1 hexane/EtOAc) gave 4-(5-difluoromethoxy-3-trifluoromethyl-pyrazol-1-yl)-benzaldehyde (350 mg, 93% yield) as a syrup.

Step 5: A stirred solution of 4-(5-difluoromethoxy-3-trifluoromethyl-pyrazol-1-yl)-benzaldehyde (40.5 mg, 0.13 mmol) and 2,3-difluorobenzylacetonitrile (20.3 mg, 0.13 mmol) in Ethanol (1 mL) was treated with 40% aqueous KOH (0.1 mL) at room temperature. The mixture was stirred for 1 hour. The resultant white precipitate was collected by filtration and washed with water to provide 5-difluoromethoxy-1-{4-[2-(2,3-difluoro-phenyl)-2-isocyano-vinyl]-phenyl}-3-trifluoromethyl-1H-pyrazole (30 mg, 51% yield) as a white solid: $^1$H-NMR (CDCl$_3$) δ 6.39 (s, 1H), 6.62 (t, 1H, J=70.8 Hz), 7.14–7.28 (m, 2H), 7.36–7.42 (m, 1H), 7.65 (s, 1H), 7.80 (d, 2H, J=8.7), 8.02 (d,2H,J=8.7) ppm. ESMS calculated for $C_{20}H_{10}F_7N_3O$: 441.1; Found: 442.0 (M+H)$^+$.

The following examples were synthesized similarly.

Compound 2: 3-[4-(5-Difluoromethoxy-3-trifluoromethyl-pyrazol-1-yl)-phenyl]-2-(2-fluoro-phenyl)-acrylonitrile $^1$H-NMR (CDCl$_3$) δ 6.32 (s,1H), 6.54 (t, 1H, J=70.8 Hz), 7.14–7.28 (m, 2H), 7.30–7.40 (m, 1H), 7.55–7.60 (m, 2H), 7.70 (d, 2H, J=8.7), 7.95 (d, 2H, J=8.7) ppm. ESMS calculated for $C_{20}H_{11}F_6N_3O$: 423.1; Found: 424.0 (M+H)$^+$.

Compound 3: 3-[4-(5-Difluoromethoxy-3-trifluoromethyl-pyrazol-1-yl)-phenyl]-2-(2,5-difluoro-phenyl)-acrylonitrile $^1$H-NMR (CDCl$_3$) δ 6.39 (s, 1H), 6.62 (t, 1H, J=70.8 Hz), 7.04–7.21 (m, 2H), 7.30–7.37 (m, 1H), 7.65 (s, 1H), 7.80 (d, 2H, J=8.7), 8.02 (d, 2H, J=8.7) ppm. ESMS calculated for $C_{20}H_{10}F_7N_3O$: 441.1; Found: 442.0 (M+H)$^+$.

Compound 4: 3-[4-(3,5-Bis-trifluoromethyl-pyrazol-1-yl)-phenyl]-2-(2,3-difluoro-phenyl)-acrylonitrile

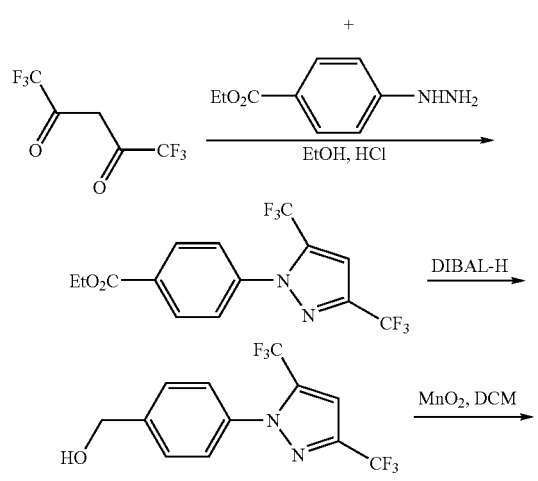

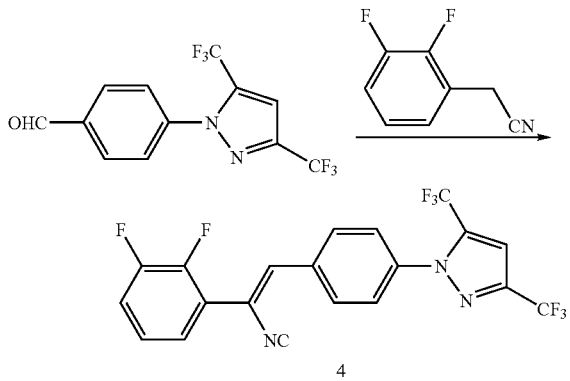

4

Step 1: A mixture of 1,1,1,5,5,5-hexafluoro-pentane-2,4-dione (3.16 g, 15.2 mmol) and 4-hydrazinobenzoic acid hydrochloride (2.86 g, 15.2 mmol) in ethanol (5 mL) was stirred at 100° C. in a sealed tube for 4 hours. The mixture was cooled to room temperature and the solvent was removed under reduced pressure. The residue was purified by chromatography ($SiO_2$, 4:1 to 3:1 hexane/EtOAc) to give 4-(3,5-bis-trifluoromethyl-pyrazol-1-yl)-benzoic acid ethyl ester, (3.1 g, 58% yield) as a syrup: $^1$H-NMR (CDCl$_3$) δ 1.40 (t, 3H, J=7), 4.35–4.50 (m, 2H), 7.10 (s, 1H), 7.60 (d, 2H, J=7), 8.21 (d, 2H, J=7) ppm.

Step 2: A stirred solution of 4-(3,5-bis-trifluoromethyl-pyrazol-1-yl)-benzoic acid ethyl ester (2.4 g, 6.8 mmol) in dry toluene (20 mL) was treated with 1M solution of DIBAL-H in toluene (10.2 mL, 10.2 mmol) at room temperature. The mixture was stirred for 1 hour and quenched with saturated aqueous $NH_4Cl$ (30 mL). The organic layer was separated and the aqueous layer was extracted with EtOAc (2×30 mL). The organics were washed with water (30 mL), dried (anhydrous $Na_2SO_4$) and the solvent removed under reduced pressure. Purification by flash chromatography ($SiO_2$, 4:1 hexane/EtOAc) gave [4-(3,5-bis-trifluoromethyl-pyrazol-1-yl)-phenyl]-methanol (2 g, 94.8% yield) as a colorless oil.

Step 3: A solution of [4-(3, 5-bis-trifluoromethyl-pyrazol-1-yl)-phenyl]-methanol (2 g) and $MnO_2$ (excess) in DCM (30 mL) was stirred at room temperature for 24 hours. Solid materials were removed by filtration and the filtrate was concentrated under reduced pressure. The resulting residue was purified by flash chromatography ($SiO_2$, 4:1 hexane/EtOAc) to give 4-(3,5-bis-trifluoromethyl-pyrazol-1-yl)-benzaldehyde (1.5 g, 76% yield) as a colorless syrup.

Step 4: A stirred solution of 4-(3,5-bis-trifluoromethyl-pyrazol-1-yl)-benzaldehyde (0.31 g, 1 mmol) and 2,3-difluorobenzylacetonitrile (0.15 g, 1 mmol) in ethanol (0.85 mL) was treated with 40% aqueous KOH (0.23 mL) in Ethanol (0.46 mL) and stirred for 1 hour. The precipitate was collected by filtration and washed with water to give 3-[4-(3,5-bis-trifluoromethyl-pyrazol-1-yl)-phenyl]-2-(2,3-difluoro-phenyl)-acrylonitrile (0.24 g, 52% yield) as a white solid: $^1$H-NMR (CDCl$_3$) δ 7.13 (s, 1H), 7.18–7.25 (m, 2H), 7.38–7.44 (m, 1H), 7.66 (d, 2H, J=8.7), 7.68 (s, 1H), 8.05 (d, 2H, J=8.7) ppm. ESMS calculated for $C_{20}H_9F8O_3$: 443.0; Found: 444.0 (M+H)$^+$.

The following examples were synthesized similarly.

Compound 5: 3-[4-(3,5-Bis-trifluoromethyl-pyrazol-1-yl)-phenyl]-2-(2,5-difluoro-phenyl)-acrylonitrile $^1$H-NMR (CDCl$_3$) δ 7.03–7.22 (m, 3H), 7.26–7.39 (m, 1H), 7.65 (d, 2H, J=8.7), 7.68 (s, 1H), 8.05 (d, 2H, J=8.7) ppm. ESMS calculated for C$_{20}$H$_9$F8O$_3$: 443.0; Found: 444.0 (M+H)$^+$.

Compound 6: 3-[4-(3,5-Bis-trifluoromethyl-pyrazol-1-yl)-phenyl]-2-(2-fluoro-phenyl)-acrylonitrile $^1$H-NMR (CDCl$_3$) δ 7.12 (s, 1H), 7.16–7.31 (m, 2H), 7.37–7.46 (m, 1H), 7.60–7.68 (m, 4H), 8.04 (d, 2H, J=8.7) ppm. ESMS calculated for C$_{20}$H$_{10}$F$_7$N$_3$: 425.1; Found: 426.0 (M+H)$^+$.

Compound 7: 3-[4-(3,5-Bis-trifluoromethyl-pyrazol-1-yl)-phenyl]-2-(2,3-difluoro-phenyl)-acrylonitrile $^1$H-NMR (CDCl$_3$) δ 7.13 (s, 1H), 7.2 (m, 3H), 7.4 (m, 1H), 7.7 (d, 2H, J=8), 8.0 (d, 2H, J=8) ppm. ESMS calculated for C$_{20}$H$_9$F$_8$N$_3$: 443.1; Found: 444.0 (M+H)$^+$.

Compound 8: 3-[4-(3,5-Bis-trifluoromethyl-pyrazol-1-yl)-phenyl]-2-(2,3,4-trifluoro-phenyl)-acrylonitrile $^1$H-NMR (DMSO-d$_6$) δ 7.6 (m, 2H), 7.8 (d, 2H, J=9), 7.92 (s, 1H), 8.02 (s, 1H), 8.1 (d, 2H, J=9) ppm. ESMS calculated for C$_{20}$H$_8$F$_9$N$_3$: 461.1; Found: 462.0 (M+H)$^+$.

Compound 9: 3-[4-(3,5-Bis-trifluoromethyl-pyrazol-1-yl)-phenyl]-2-(2,3,6-trifluoro-phenyl)-acrylonitrile $^1$H-NMR (CDCl$_3$) δ 7.0 (m, 1H), 7.14 (s, 1H), 7.3 (m, 1H), 7.42 (s, 1H), 7.7 (d, 2H, J=9), 8.1 (d, 2H, J=9) ppm. ESMS calculated for C$_{20}$H$_8$F$_9$N$_3$: 461.1; Found: 462.0 (M+H)$^+$.

Compound 10: 3-[4-(3,5-Bis-trifluoromethyl-pyrazol-1-yl)-phenyl]-2-(3,4,5-trifluoro-phenyl)-acrylonitrile $^1$H-NMR (CDCl$_3$) δ 7.14 (s, 1H), 7.4 (m, 2H), 7.53 (s, 1H), 7.7 (d, 2H, J=9), 8.1 (d, 2H, J=9) ppm. ESMS calculated for C$_{20}$H$_8$F$_9$N$_3$: 461.1; Found: 462.1 (M+H)$^+$.

Compound 11: 3-[4-(3,5-Bis-trifluoromethyl-pyrazol-1-yl)-phenyl]-2-(2,3,5-trifluoro-phenyl)-acrylonitrile $^1$H-NMR (CDCl$_3$) δ 7.0 (m, 1H), 7.13 (s, 1H), 7.2 (m, 1H), 7.7 (d, 2H, J=9), 7.70 (s, 1H), 8.1 (d, 2H, J=9) ppm. ESMS calculated for C$_{20}$H$_8$F$_9$N$_3$: 461.1; Found: 462.0 (M+H)$^+$.

Compound 12: 3-[4-(3,5-Bis-trifluoromethyl-pyrazol-1-yl)-phenyl]-2-(3,4,6-trifluoro-phenyl)-acrylonitrile $^1$H-NMR (CDCl$_3$) ι 7.1 (m, 1H), 7.13 (s, 1H), 7.5 (m, 1H), 7.62 (s, 1H), 7.7 (d, 2H, J=9), 8.0 (d, 2H, J=9) ppm. ESMS calculated for C$_{20}$H$_8$F$_9$N$_3$: 461.1; Found: 462.0 (M+H)$^+$.

Compound 13: 3-[4-(3,5-Bis-trifluoromethyl-pyrazol-1-yl)-2-chloro-phenyl]-2-(2,3-difluoro-phenyl)-acrylonitrile $^1$H-NMR (CDCl$_3$) δ 7.14 (s, 1H), 7.2 (m, 2H), 7.4 (m, 1H), 7.6 (m, 1H), 7.7 (d, 1H, J=3), 7.99 (s, 1H), 8.3 (d, 1H, J=9) ppm. ESMS calculated for C$_{20}$H$_8$ClF$_8$N$_3$: 477.0; Found: 478.3 (M+H)$^+$.

Compound 14: 3-[2-(3,5-Bis-trifluoromethyl-pyrazol-1-yl)-phenyl]-2-(2,3-difluoro-phenyl)-acrylonitrile $^1$H-NMR (CDCl$_3$) δ 7.0–7.3 (m, 4H), 7.5–7.8 (m, 4H), 8.34 (d, 1H, J=8 ppm. ESMS calculated for C$_{20}$H$_9$F8O$_3$: 443.0; Found: 444.0 (M+H)$^+$.

Compound 15: 2-(2,5-Difluoro-phenyl)-3-[4-(3-methyl-5-trifluoromethyl-pyrazol-1-yl)-phenyl]-acrylonitrile

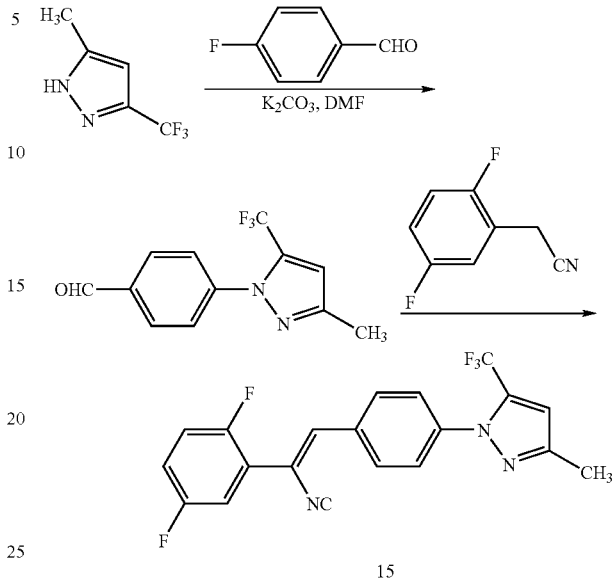

To a solution of 4-fluorobenzaldehyde (0.43 mL, 4.03 mmol) and 3-methyl-5-trifluoro-pyrazole (727 mg, 4.84 mmol) in DMF (5 mL) was added potassium carbonate (0.67 g, 4.84 mmol) and the mixture was heated at 120° C. for 14 hours. The mixture was diluted with water (50 mL) and extracted with EtOAc. The organic layer was washed with water and brine, dried (anhydrous MgSO$_4$), evaporated, and purified by chromatography (SiO$_2$, 4:1 Hexane/EtOAc) to give 4-(3-methyl-5-trifluoromethyl-pyrazol-1-yl)-benzaldehyde (0.87 g, 85% yield) as a yellow oil: $^1$H-NMR (CDCl$_3$) δ 2.44 (s, 3H), 6.51 (s, 1H), 7.7 (d, 2H, J=9), 8.1 (d, 2H, J=9), 10.10 (s, 1H) ppm. ESMS calculated for C$_{12}$H$_9$F$_3$N$_2$O: 254.1; Found: 255.0 (M+H)$^+$.

To a stirred mixture of 4-(3-methyl-5-trifluoromethyl-pyrazol-1-yl)-benzaldehyde (127 mg, 0.50 mmol) and 2,5-difluoro-phenylacetonitrile (77 mg, 0.50 mmol) in ethanol (4 mL) was added 0.5 mL of aqueous 6N KOH at room temperature. The mixture was stirred for 2 hours and the resulting precipitate was collected by filtration to give 2-(2,5-difluoro-phenyl)-3-[4-(3-methyl-5-trifluoromethyl-pyrazol-1-yl )-phenyl]-acrylonitrile (170 mg, 87% yield) as a white solid: $^1$H-NMR (CDCl$_3$) δ 2.45 (s, 3H), 6.51 (s, 1H), 7.1 (m, 2H), 7.3 (m, 1H), 7.6 (d, 2H, J=9), 7.67 (s, 1H), 8.0 (d, 2H, J=9) ppm. ESMS calculated for C$_{20}$H$_{12}$F$_5$N$_3$: 389.1; Found: 390.0 (M+H)$^+$.

The following examples were synthesized similarly.

Compound 16: 2-(2,4-Difluoro-phenyl)-3-[4-(3-trifluoromethyl-pyrazol-1-yl)-phenyl]-acrylonitrile $^1$H-NMR (DMSO-d$_6$) δ 7.12 (d, 1H, J=2), 7.3 (m, 1H), 7.5 (m, 1H), 7.8 (m, 1H), 7.87 (s, 1H), 8.0 (m, 4H), 8.87 (d, 1H, J=2) ppm. ESMS calculated for C$_{19}$H$_{10}$F$_5$N$_3$: 375.1; Found: 376.0 (M+H)$^+$.

Compounds 17: 2-(2,3-Difluoro-phenyl)-3-[4-(3-trifluoromethyl-pyrazol-1-yl)-phenyl]-acrylonitrile $^1$H-NMR (DMSO-d$_6$) δ 7.12 (d, 1H, J=3), 7.4 (m, 1H), 7.5 (m, 1H), 7.97 (s, 1H), 8.1 (m, 5H), 8.87 (d, 1H, J=3) ppm. ESMS calculated for C$_{19}$H$_{10}$F$_5$N$_3$: 375.1; Found: 376.0 (M+H)$^+$.

Compound 18: 2-(2,3-Difluoro-phenyl)-3-[4-(3-methyl-5-trifluoromethyl-pyrazol-1-yl)-phenyl]-acrylonitrile ¹H-NMR (CDCl₃) δ 2.45 (s, 3H), 6.51 (s, 1H), 7.2 (m, 2H), 7.4 (m, 1H), 7.6 (d, 2H, J=8), 7.67 (s, 1H), 8.0 (d, 2H, J=8) ppm. ESMS calculated for $C_{20}H_{12}F_5N_3$: 389.1 Found: 390.0 $(M+H)^+$.

Compound 19: 2-(2,4-Difluoro-phenyl)-3-[4-(3-methyl-5-trifluoromethyl-pyrazol-1-yl)-phenyl]-acrylonitrile ¹H-NMR (CDCl₃) δ 2.44 (s, 3H), 6.51 (s, 1H), 6.9 (m, 2H), 7.6 (m, 4H), 8.0 (d, 2H, J=9) ppm. ESMS calculated for $C_{20}H_{12}F_5N_3$: 389.1; Found: 390.1 $(M+H)^+$.

Compound 20: 2-(2,6-Difluoro-phenyl)-3-[4-(3-methyl-5-trifluoromethyl-pyrazol-1-yl)-phenyl]-acrylonitrile ¹H-NMR (CDCl₃) δ 2.44 (s, 3H), 6.51 (s, 1H), 7.0 (t, 2H, J=8), 7.4 (m, 2H), 7.6 (d, 2H, J=9), 8.0 (d, 2H, J=9) ppm. ESMS calculated for $C_{20}H_{12}F_5N_3$: 389.1; Found: 390.1 $(M+H)^+$.

Compound 21: 2-(3,4-Difluoro-phenyl)-3-[4-(3-methyl-5-trifluoromethyl-pyrazol-1-yl)-phenyl]-acrylonitrile ¹H-NMR (CDCl₃) δ 2.45 (s, 3H), 6.51 (s, 1H), 7.3 (m, 1H), 7.5 (m, 3H), 7.6 (d, 2H, J=8), 8.0 (d, 2H, J=8) ppm. ESMS calculated for $C_{20}H_{12}F_5N_3$: 389.1; Found: 390.0 $(M+H)^+$.

Compound 22: 2-(3,5-Difluoro-phenyl)-3-[4-(3-methyl-5-trifluoromethyl-pyrazol-1-yl)-phenyl]-acrylonitrile ¹H-NMR (CDCl₃) δ 2.45 (s, 3H), 6.52 (s, 1H), 6.9 (m, 1H), 7.3 (m, 2H), 7.60 (s, 1H), 7.6 (d, 2H, J=8), 8.0 (d, 2H, J=8) ppm. ESMS calculated for $C_{20}H_{12}F_5N_3$: 389.1; Found: 390.1 $(M+H)^+$.

Compound 23: 2-Phenyl-3-(4-pyrazol-1-yl-phenyl)-acrylonitrile

¹H-NMR (CDCl₃) δ 6.51–6.54 (m, 1H), 7.40–7.51 (m, 3H), 7.54 (s, 1H), 7.66–7.73 (m, 2H), 7.77 (d, 1H, J=1.2), 7.80–7.86 (m, 2H), 7.98–8.05 (m, 3H) ppm. ESMS calculated for $C_{18}H_{13}N_3$: 271.1; Found: 272.0 $(M+H)^+$.

Compound 24: 2-(2,5-Difluoro-phenyl)-3-(4-pyrazol-1-yl-phenyl)-acrylonitrile

¹H-NMR (CDCl₃) δ 6.51–6.56 (m, 1H), 7.04–7.22 (m, 2H), 7.28–7.38 (m, 1H), 7.62 (s, 1H), 7.77 (s, 1H), 7.85 (d, 2H, J=8), 8.00(s, 1H), 8.04 (d, 2H, J=8) ppm. ESMS calculated for $C_{18}H_{11}F2N_3$: 307.1; Found: 308.0 $(M+H)^+$.

Compound 25: 3-[4-(3,5-Bis-trifluoromethyl-pyrazol-1-yl)-phenyl]-2-(2,3-difluoro-benzoyl)-acrylonitrile

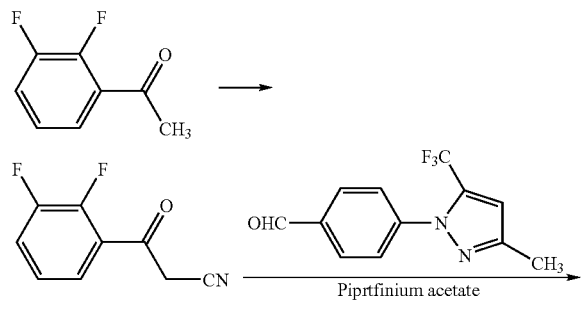

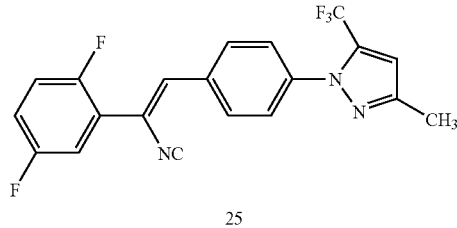

A stirred solution of 2,3-difluoroacetophenone (5.40 g, 34.6 mmol) in EtOAc (100 mL) was treated dropwise with bromine (1.77 mL, 34.6 mmol) at room temperature and the mixture was stirred for 30 minutes. The solvent was removed under reduced pressure to give the intermediate bromide as a yellow oil. The oil was dissolved in DMF (60 mL), cooled to 0° C. and treated with NaCN (2.94 g, 60 mmol) and stirred for 2 hours. The mixture was acidified with aqueous 5% citric acid (100 mL) and extracted with EtOAc. The organic layer was dried (anhydrous MgSO₄), evaporated, and purified by chromatography (SiO₂, 4:1 hexane/EtOAc) to give 3-(2,3-difluoro-phenyl)-3-oxo-propionitrile (1.19 g, 19% yield) as a yellow solid: ¹H-NMR (CDCl₃) δ 4.08 (s, 2H), 7.2 (m, 1H), 7.5 (m, 1H), 7.7 (m, 1H) ppm. ESMS calculated for $C_9H_5F_2NO$: 181.0; Found: 182.0 $(M+H)^+$.

A stirred solution of 4-(3,5-bis-trifluoromethyl-pyrazol-1-yl)-benzaldehyde (0.18 g, 0.58 mmol), 3-(2,3-difluoro-phenyl)-3-oxo-propionitrile (0.1 g, 0.55 mmol) and piperidine acetate (8 mg, 0.06 mmol) in dry benzene was heated at reflux for 12 hours. Volatile components were removed under reduced pressure to give a syrup. Trituration with ether gave 3-[4-(3,5-bis-trifluoromethyl-pyrazol-1-yl)-phenyl]-2-(2,3-difluoro-benzoyl)-acrylonitrile (0.18 g, 65% yield) as a solid: ¹H-NMR (CDCl₃) δ 7.15 (s, 1H), 7.24–7.32 (m, 1H), 7.38–7.50 (m, 2H), 7.72 (d, 2H, J=8.4), 8.11 (s, 1H), 8.20 (d, 2H, J=8.4) ppm. ESMS calculated for $C_{21}H_9F_8N_3O$: 471.1; Found: 472.0 $(M+H)^+$.

The following examples were synthesized similarly.

Compound 26: 2-Benzoyl-3-[4-(5-trifluoromethyl-pyrazol-1-yl)-phenyl]-acrylonitrile ¹H-NMR (CDCl₃) δ 6.80 (d, 1H, J=2.4), 7.20 (d, 1H, J=9), 7.50–7.58 (m, 2H), 7.62–7.73 (m, 1H), 7.89–7.94 (m, 1H), 7.92 (d, 2H, J=9), 8.03–8.14 (m, 2H), 8.18 (d, 2H, J=8.7) ppm. ESMS calculated for $C_{20}H_{12}F_3N_3O$: 367.1; Found: 368.1 $(M+H)^+$.

Compound 27: 2-(Furan-2-carbonyl)-3-[4-(5-trifluoromethyl-pyrazol-1-yl)-phenyl]-acrylonitrile ¹H-NMR (CDCl₃) δ 6.65–6.70 (m, 1H), 6.80 (d, 1H, J=2.1), 7.21 (d, 11H, J=9), 7.78 (d, 2H, J=4.2), 7.92 (d, 2H, J=8.7), 8.05–8.18 (m, 1H), 8.20 (d, 2H, J=8.7), 8.37 (bs, 1H) ppm. ESMS calculated for $C_{18}H_{10}F_3N_2O_2$: 357.1; Found: 358.0 $(M+H)^+$.

Compound 28: 2-Benzoyl-3-[4-(3-thiophen-2-yl-pyrazol-1-yl)-phenyl]-acrylonitrile ¹H-NMR (CDCl₃) δ 6.78 (s, 1H), 7.11 (s, 1H), 7.30–7.38 (m, 1H), 7.42–7.70 (m, 4H), 7.85–7.98 (m, 4H), 8.06 (d, 2H, J=9), 8.16 (d, 2H, J=7) ppm. ESMS calculated for $C_{23}H_{15}N_3OS$: 381.1; Found: 382.0 $(M+H)^+$.

Compound 29: 2-(Furan-2-carbonyl)-3-[4-(3-methyl-pyrazol-1-yl)-phenyl]-acrylonitrile $^1$H-NMR (CDCl$_3$) δ 2.40 (s, 3H), 6.33 (d, 1H, J=2.1), 6.65 (dd, 1H, J=1.8; 3.0), 7.76 (m, 1H), 7.78 (d, 1H, J=3.9), 7.84 (d, 2H, J=9), 7.94 (d, 1H, J=2.4), 8.18 (d, 2H, J=9), 8.37 (s, 1H)ppm. ESMS calculated for C$_{18}$H$_{13}$N$_3$O$_2$: 303.1; Found: 304.0 (M+H)$^+$.

Compound 30: 2-Benzoyl-3-(4-pyrazol-1-yl-phenyl)-acrylonitrile $^1$H-NMR (CDCl$_3$) δ 6.54 (dd, 1H, J=1.8; 2.0), 7.54 (t, 2H, J=7.5), 7.65 (t,1H, J=7.2), 7.79 (d, 1H, J=1.2), 7.86–7.94 (m, 4H), 8.04 (d, 2H, J=2.4), 8.16 (d, 2H, J=8.7) ppm. ESMS calculated for C$_{19}$H$_{13}$N$_3$O: 299.1; Found: 300.0 (M+H)$^+$.

Compound 31: 2-(Furan-2-carbonyl)-3-[4-(3-phenyl-pyrazol-1-yl)-phenyl]-acrylonitrile $^1$H-NMR (CDCl$_3$) δ 6.66 (dd, 1H, J=1.8; 3.8), 6.86 (d, 1H, J=2.4), 7.38 (t, 2H, J=7), 7.46 (t, 2H, J=7), 7.77 (s, 1H), 7.79 (d, 1H, J=3.6), 7.94 (d, 1H, J=7), 7.97 (d, 2H, J=9), 8.08 (d, 1H, J=2.7), 8.21 (d, 2H, J=8), 8.39 (s, 1H)ppm. ESMS calculated for C$_{23}$H$_{15}$N$_3$O$_2$: 365.1; Found: 366.0 (M+H)$^+$.

Compound 32: 3-[4-(3,5-Bis-trifluoromethyl-pyrazol-1-yl)-phenyl]-2-(2,3-difluoro-benzoyl)-acrylonitrile $^1$H-NMR (CDCl$_3$) δ 7.15 (s, 1H), 7.24–7.32 (m, 1H), 7.38–7.50 (m, 2H), 7.72 (d, 2H, J=8.4), 8.11 (s, 1H), 8.20 (d, 2H, J=8.4) ppm. ESMS calculated for C$_{21}$H$_9$F$_8$N$_3$O: 471.1; Found: 472.0 (M+H)$^+$.

Compound 33: 3-[4-(3,5-Bis-trifluoromethyl-pyrazol-1-yl)-phenyl]-2-(furan-2-carbonyl)-acrylonitrile $^1$H-NMR (CDCl$_3$) δ 6.68 (dd, 1H, J=2.1; 3.6), 7.15 (s, 1H), 7.72 (d, 2H, J=8.7), 7.79 (s, 1H), 7.80 (d, 1H, J=5), 8.21 (d, 2H, J=8.7), 8.04 (bs, 1H) ppm. ESMS calculated for C$_{19}$H$_9$F$_6$N$_3$O$_2$: 425.1; Found: 426.0 (M+H)$^+$.

Compound 34: 3-[4-(3,5-Bis-trifluoromethyl-pyrazol-1-yl)-phenyl]-2-(2,4-difluoro-benzoyl)-acrylonitrile $^1$H-NMR (CDCl$_3$) δ 6.82–7.12 (m, 2H), 7.15 (s, 1H), 7.67–7.76 (m, 3H), 8.10 (s, 1H), 8.15–8.23 (m, 2H) ppm. ESMS calculated for C$_{21}$H$_9$F$_8$N$_3$O: 471.1; Found: 472.0 (M+H)$^+$.

Compound 35: 2-(2,3-Difluoro-benzoyl)-3-[4-(3-phenyl-pyrazol-1-yl)-phenyl]-acrylonitrile $^1$H-NMR (CDCl$_3$) δ 6.87 (d, 1H, J=2.7), 7.22–7.31 (m, 1H), 7.34–7.50 (m, 5H), 7.91–7.97 (m, 2H), 7.98 (d, 2H, J=8.7), 8.09 (d, 2H, J=2.4), 8.20 (d, 2H, J=8.7) ppm. ESMS calculated for C$_{25}$H$_{15}$F$_2$N$_3$O: 411.1; Found: 412.1 (M+H)$^+$.

Compound 36: 2-(2,3-Difluoro-benzoyl)-3-[4-(3-methyl-5-trifluoromethyl-pyrazol-1-yl)-phenyl]-acrylonitrile $^1$H-NMR (CDCl$_3$) δ 2.46 (s, 3H), 6.56 (s, 1H), 7.3 (m, 1H), 7.4 (m, 2H), 7.7 (d, 2H, J=9), 8.10 (s, 1H), 8.2 (d, 2H, J=9) ppm. ESMS calculated for C$_{21}$H$_{12}$F$_5$N$_3$O: 417.1; Found: 418.1 (M+H)$^+$.

Compound 37: 2-(2,4-Difluoro-benzoyl)-3-[4-(3-trifluoromethyl-pyrazol-1-yl)-phenyl]-acrylonitrile $^1$H-NMR (CDCl$_3$) δ 6.81 (s, 1H), 7.0 (m, 2H), 7.7 (m, 1H), 7.9 (d, 1H, J=9), 8.1 (d, 2H, J=7), 8.2 (d, 2H, J=9) ppm. ESMS calculated for C$_{20}$H$_{10}$F$_5$N$_3$O: 403.1; Found: 404.0 (M+H)$^+$.

Compound 38: 2-(2,3-Difluoro-benzoyl)-3-[4-(3-trifluoromethyl-pyrazol-1-yl)-phenyl]-acrylonitrile $^1$H-NMR (CDCl$_3$) δ 6.80 (s, 1H), 7.2–7.5 (m, 3H), 7.9 (d, 1H, J=9), 8.1 (d, 2H, J=7), 8.2 (d, 2H, J=9) ppm. ESMS calculated for C$_{20}$H$_{10}$F$_5$N$_3$O: 403.1; Found: 404.0 (M+H)$^+$.

Compound 39: 2-(2,4-Difluoro-benzoyl)-3-[4-(3-methyl-5-trifluoromethyl-pyrazol-1-yl)-phenyl]-acrylonitrile $^1$H-NMR (CDCl$_3$) δ 2.48 (s, 3H), 6.56 (s, 1H), 7.0 (m, 2H), 7.7 (m, 3H), 8.10 (s, 1H), 8.2 (d, 2H, J=9) ppm. ESMS calculated for C$_{21}$H$_{12}$F$_5$N$_3$O: 417.1; Found: 418.0 (M+H)$^+$.

Compound 40: 2-(2,5-Difluoro-benzoyl)-3-[4-(3-methyl-5-trifluoromethyl-pyrazol-1-yl)-phenyl]-acrylonitrile $^1$H-NMR (CDCl$_3$) δ 2.44 (s, 3H), 6.58 (s, 1H), 7.2–7.4 (m, 3H), 7.7 (d, 2H, J=9), 8.10 (s, 1H), 8.2 (d, 2H, J=9) ppm. ESMS calculated for C$_{21}$H$_{12}$F$_5$N$_3$O: 417.1; Found: 418.0 (M+H)$^+$.

Compound 41: 2-(2,5-Difluoro-benzoyl)-3-[4-(3-trifluoromethyl-pyrazol-1-yl)-phenyl]-acrylonitrile $^1$H-NMR (CDCl$_3$) δ 6.80 (s, 1H), 7.2–7.4 (m, 3H), 7.9 (d, 2H, J=9), 8.08 (s, 1H), 8.2 (d, 2H, J=9) ppm. ESMS calculated for C$_{20}$H$_{10}$F$_5$N$_3$O: 403.1; Found: 404.0 (M+H)$^+$.

Compound 42

2-(2,5-Difluoro-phenyl)-3-[4-(3-trifluoromethyl-pyrazol-1-yl)-phenyl]-acrylonitrile $^1$H-NMR (CDCl$_3$) δ 6.8 (d, 1H, J=6), 7.1 (m, 2H), 7.4 (m, 1H), 7.65 (s, 1H), 7.9 (d, 2H, J=8), 8.0 (m, 3H) ppm. ESMS calcd for C$_{19}$H$_{10}$F$_5$N$_3$: 375.1; Found: 376.0 (M+H)$^+$.

Compound 43

3-[3-(3,5-Bis-trifluoromethyl-pyrazol-1-yl)-phenyl]-2-(2,3-difluoro-phenyl)-acryl onitrile $^1$H-NMR (CDCl$_3$) δ 7.13 (s, 1H), 7.2 (m, 2H), 7.4 (m, 1H), 7.7 (m, 3H), 7.9 (m, 1H), 8.2 (m, 1H) ppm. ESMS calcd for C$_{20}$H$_9$F$_8$N$_3$: 443.1; Found: 444.0 (M+H)$^+$.

Compound 44

3-[3-(3,5-Bis-trifluoromethyl-pyrazol-1-yl)-phenyl]-2-(2,5-difluoro-phenyl)-acryl onitrile $^1$H-NMR (CDCl$_3$) δ 7.13 (s, 1H), 7.1 (m, 2H), 7.4 (m, 1H), 7.7 (m, 3H), 8.0 (m, 1H), 8.2 (m, 1H) ppm. ESMS calcd for C$_{20}$H$_9$F$_8$N$_3$: 443.1; Found: 444.0 (M+H)$^+$.

Compound 45

2-(2,3-Difluoro-phenyl)-3-[4-(2-trifluoromethyl-benzoimidazol-1-yl)-phenyl]-acry lonitrile $^1$H-NMR (CDCl$_3$) δ 7.2 (m, 3H), 7.4 (m, 3H), 7.6 (m, 2H), 7.72 (s, 1H), 8.0 (m, 1H), 8.1 (m, 2H) ppm. ESMS calcd for C$_{23}$H$_{12}$F$_5$N$_3$: 425. 1; Found: 426.1 (M+H)$^+$.

Compound 46

2-(2,5-Difluoro-phenyl)-3-[4-(2-trifluoromethyl-benzoimidazol-1-yl)-phenyl]-acry lonitrile $^1$H-NMR (CDCl$_3$) δ 7.2 (m, 3H), 7.4 (m, 1H), 7.5 (m, 2H), 7.6 (m, 2H), 7.76 (s, 1H), 8.0 (m, 1H), 8.2 (m, 2H) ppm. ESMS calcd for C$_{23}$H$_{12}$F$_5$N$_3$: 425.1; Found: 426.1 (M+H)$^+$.

Compound 47

3-[4-(3,5-Bis-trifluoromethyl-pyrazol-1-yl)-phenyl]-2-(3,4-difluoro-benzoyl)-acrylonitrile $^1$H-NMR (CDCl$_3$) δ 7.13 (s, 1H), 7.40 (m, 1H), 7.44–7.58 (m, 3H), 7.65 (d, 2H, J=9), 8.2 (d, 2H, J=9) ppm. ESMS calcd for C$_{21}$H$_9$F$_8$N$_3$O: 471.1; Found: 472.1 (M+H)$^+$.

Compound 48

2-(2-Fluoro-phenyl)-3-(4-pyrazol-1-yl-phenyl)-acrylonitrile $^1$H-NMR (CDCl$_3$) δ 6.53–6.55 (m, 1H), 7.39–7.52 (m, 3H), 7.54 (s, 1H), 7.64–7.74 (m, 2H), 7.78 (d, 1H, J=2), 7.80–7.86 (m, 1H), 7.99–8.10 (m, 3H)ppm. ESMS calcd for C$_{18}$H$_{12}$FN$_3$: 289.1; Found: 290.1 (M+H)$^+$.

Compound 49

2-(2,5-Difluoro-cyclohexa-2,4-dienyl)-3-[4-(3-methyl-pyrazol-1-yl)-phenyl]-acrylonitrile $^1$H-NMR (CDCl$_3$)δ 2.40 (s, 3H), 6.30 (d, 1H, J=2), 7.01–7.20 (m, 2H), 7.25–7.35 (m, 1H), 7.60 (s, 1H), 7.81 (d, 2H, J=9), 7.90-(d, 1H, J=2), 8.00 (d, 2H, J=9)ppm. ESMS calcd for C$_{19}$H$_{13}$F$_2$N$_3$: 321.1; Found: 322.0 (M+H)$^+$.

Example 2

Compounds of the Present Invention Inhibit IL-2 Production on a Human Jurkat Cell Line Jurkat cells (ATCC, Cat# TIB-152) were grown in RPMI1640 medium (ATCC, Cat# 30-2001) containing 10% of FBS (ATCC, Cat# 30-2020). For compound screening, Jurkat cells were plated in 96-well plates at a density of 0.5 million cells per well in RPMI1640 medium containing 1% of FBS. Then, various concentrations of each test compound were added to the cell plates followed by addition of PHA (Sigma, Cat# L-9017) at a final concentration of 2.5 µg/ml to stimulate IL-2 production. Cells were then incubated at 37° C. (±5% CO$_2$) for 20 hours before ELISA assay. After 20 hours incubation, cell plates were centrifuged at 500–800 g for 5 minutes and the supernatants was collected for IL-2 detection using the human IL-2 ELISA kit purchased from Cell Sciences (Cat# 851.500.020). The ELISA assay for IL-2 production was done in 96-well plates using a protocol provided by Cell Sciences.

The IC$_{50}$ (i.e., the concentration at which IL-2 release is inhibited by 50%) was determined and the results are shown in the Table. As can be seen from these results, compounds of the present invention are effective at inhibiting IL-2 release. The designation "A" means an IC$_{50}$ less than 0.010 µM; the designation B means an IC$_{50}$ between 0.010 and 1.0 µM; and the designation "C" mean an IC$_{50}$ greater than 1 µM.

THE TABLE

| Cpd. No. | $R^1$ / $R^2$ | Cy$^1$—(R$^3$)$_n$ | Y | IC$_{50}$ (µM) | Chemical Name |
|---|---|---|---|---|---|
| 26 | benzoyl | phenylene | 3-CF$_3$-pyrazol-1-yl | C | 2-Benzoyl-3-[4-(5-trifluoromethyl-pyrazol-1-yl)-phenyl]-acrylonitrile |
| 27 | furan-2-carbonyl | phenylene | 3-CF$_3$-pyrazol-1-yl | C | 2-(Furan-2-carbonyl)-3-[4-(5-trifluoromethyl-pyrazol-1-yl)-phenyl]-acrylonitrile |
| 28 | benzoyl | phenylene | 3-(thiophen-2-yl)-pyrazol-1-yl | C | 2-Benzoyl-3-[4-(3-thiophen-2-yl-pyrazol-1-yl)-phenyl]-acrylonitrile |
| 23 | phenyl | phenylene | pyrazol-1-yl | C | 2-Phenyl-3-(4-pyrazol-1-yl-phenyl)-acrylonitrile |

THE TABLE-continued

| Cpd. No. | R¹ R² | Cy¹—(R³)ₙ | Y | IC$_{50}$ (μM) | Chemical Name |
|---|---|---|---|---|---|
| 29 | furan-2-carbonyl | phenylene | 3-methyl-pyrazol-1-yl | C | 2-(Furan-2-carbonyl)-3-[4-(3-methyl-pyrazol-1-yl)-phenyl]-acrylonitrile |
| 30 | benzoyl | phenylene | pyrazol-1-yl | C | 2-Benzoyl-3-(4-pyrazol-1-yl-phenyl)-acrylonitrile |
| 31 | furan-2-carbonyl | phenylene | 3-phenyl-pyrazol-1-yl | C | 2-(Furan-2-carbonyl)-3-[4-(3-phenyl-pyrazol-1-yl)-phenyl]-acrylonitrile |
| 4 | 2,3-difluorophenyl | phenylene | 3,5-bis-trifluoromethyl-pyrazol-1-yl | A | 3-[4-(3,5-Bis-trifluoromethyl-pyrazol-1-yl)-phenyl]-2-(2,3-difluoro-phenyl)-acrylonitrile |
| 37 | 2,4-difluorobenzoyl | phenylene | 3-trifluoromethyl-pyrazol-1-yl | C | 2-(2,4-Difluoro-benzoyl)-3-[4-(3-trifluoromethyl-pyrazol-1-yl)-phenyl]-acrylonitrile |
| 38 | 2,3-difluorobenzoyl | phenylene | 3-trifluoromethyl-pyrazol-1-yl | C | 2-(2,3-Difluoro-benzoyl)-3-[4-(3-trifluoromethyl-pyrazol-1-yl)-phenyl]-acrylonitrile |
| 25 | 2,3-difluorobenzoyl | phenylene | 3,5-bis-trifluoromethyl-pyrazol-1-yl | C | 3-[4-(3,5-Bis-trifluoromethyl-pyrazol-1-yl)-phenyl]-2-(2,3-difluoro-benzoyl)-acrylonitrile |

THE TABLE-continued

| Cpd. No. | R¹ R² | Cy¹—(R³)$_n$ | Y | IC$_{50}$ (μM) | Chemical Name |
|---|---|---|---|---|---|
| 33 | furan-2-carbonyl | phenyl | 3,5-bis-CF₃-pyrazol-1-yl | C | 3-[4-(3,5-Bis-trifluoromethyl-pyrazol-1-yl)-phenyl]-2-(furan-2-carbonyl)-acrylonitrile |
| 36 | 2,3-difluorobenzoyl | phenyl | 3-CH₃-5-CF₃-pyrazol-1-yl | C | 2-(3,4-Difluoro-benzoyl)-3-[4-(3-methyl-5-trifluoromethyl-pyrazol-1-yl)-phenyl]-acrylonitrile |
| 34 | 2,4-difluorobenzoyl | phenyl | 3,5-bis-CF₃-pyrazol-1-yl | C | 3-[4-(3,5-Bis-trifluoromethyl-pyrazol-1-yl)-phenyl]-2-(2,4-difluoro-benzoyl)-acrylonitrile |
| 39 | 2,4-difluorobenzoyl | phenyl | 3-CH₃-5-CF₃-pyrazol-1-yl | C | 2-(2,4-Difluoro-benzoyl)-3-[4-(3-methyl-5-trifluoromethyl-pyrazol-1-yl)-phenyl]-acrylonitrile |
| 35 | 2,3-difluorobenzoyl | phenyl | 3-phenyl-pyrazol-1-yl | C | 2-(2,3-Difluoro-benzoyl)-3-[4-(3-phenyl-pyrazol-1-yl)-phenyl]-acrylonitrile |
| 40 | 2,5-difluorobenzoyl | phenyl | 3-CH₃-5-CF₃-pyrazol-1-yl | C | 2-(2,5-Difluoro-benzoyl)-3-[4-(3-methyl-5-trifluoromethyl-pyrazol-1-yl)-phenyl]-acrylonitrile |

THE TABLE-continued

| Cpd. No. | R¹ R² | Cy¹—(R³)ₙ | Y | IC$_{50}$ (μM) | Chemical Name |
|---|---|---|---|---|---|
| 41 | 2,5-difluorobenzoyl | phenylene | 3-trifluoromethyl-pyrazol-1-yl | C | 2-(2,5-Difluoro-benzoyl)-3-[4-(3-trifluoromethyl-pyrazol-1-yl)-phenyl]-acrylonitrile |
| 5 | 2,5-difluorophenyl | phenylene | 3,5-bis-trifluoromethyl-pyrazol-1-yl | A | 3-[4-(3,5-Bis-trifluoromethyl-pyrazol-1-yl)-phenyl]-2-(2,5-difluoro-phenyl)-acrylonitrile |
| 47 | 3,4-difluorophenyl | phenylene | 3,5-bis-trifluoromethyl-pyrazol-1-yl | B | 3-[4-(3,5-Bis-trifluoromethyl-pyrazol-1-yl)-phenyl]-2-(2,3-difluoro-phenyl)-acrylonitrile |
| 16 | 2,4-difluorophenyl | phenylene | 3-trifluoromethyl-pyrazol-1-yl | C | 2-(2,4-Difluoro-phenyl)-3-[4-(3-trifluoromethyl-pyrazol-1-yl)-phenyl]-acrylonitrile |
| 17 | 2,3-difluorophenyl | phenylene | 3-trifluoromethyl-pyrazol-1-yl | C | 2-(2,3-Difluoro-phenyl)-3-[4-(3-trifluoromethyl-pyrazol-1-yl)-phenyl]-acrylonitrile |
| 18 | 2,3-difluorophenyl | phenylene | 3-methyl-5-trifluoromethyl-pyrazol-1-yl | B | 2-(2,3-Difluoro-phenyl)-3-[4-(3-methyl-5-trifluoromethyl-pyrazol-1-yl)-phenyl]-acrylonitrile |
| 3 | 2,5-difluorophenyl | phenylene | 5-difluoromethoxy-3-trifluoromethyl-pyrazol-1-yl | B | 3-[4-(5-Difluoromethoxy-3-trifluoromethyl-pyrazol-1-yl)-phenyl]-2-(2,5-difluoro-phenyl)-acrylonitrile |

THE TABLE-continued

| Cpd. No. | R¹ R² | Cy¹—(R³)ₙ | Y | IC₅₀ (μM) | Chemical Name |
|---|---|---|---|---|---|
| 19 | 2,4-difluorophenyl | phenyl | 3-methyl-5-trifluoromethyl-pyrazol-1-yl | B | 2-(2,4-Difluoro-phenyl)-3-[4-(3-methyl-5-trifluoromethyl-pyrazol-1-yl)-phenyl]-acrylonitrile |
| 15 | 2,5-difluorophenyl | phenyl | 3-methyl-5-trifluoromethyl-pyrazol-1-yl | B | 2-(2,5-Difluoro-phenyl)-3-[4-(3-methyl-5-trifluoromethyl-pyrazol-1-yl)-phenyl]-acrylonitrile |
| 20 | 2,6-difluorophenyl | phenyl | 3-methyl-5-trifluoromethyl-pyrazol-1-yl | B | 2-(2,6-Difluoro-phenyl)-3-[4-(3-methyl-5-trifluoromethyl-pyrazol-1-yl)-phenyl]-acrylonitrile |
| 21 | 3,4-difluorophenyl | phenyl | 3-methyl-5-trifluoromethyl-pyrazol-1-yl | B | 2-(3,4-Difluoro-phenyl)-3-[4-(3-methyl-5-trifluoromethyl-pyrazol-1-yl)-phenyl]-acrylonitrile |
| 22 | 3,5-difluorophenyl | phenyl | 3-methyl-5-trifluoromethyl-pyrazol-1-yl | B | 2-(3,5-Difluoro-phenyl)-3-[4-(3-methyl-5-trifluoromethyl-pyrazol-1-yl)-phenyl]-acrylonitrile |
| 1 | 2,3-difluorophenyl | phenyl | 5-difluoromethoxy-3-trifluoromethyl-pyrazol-1-yl | B | 3-[4-(5-Difluoromethoxy-3-trifluoromethyl-pyrazol-1-yl)-phenyl]-2-(2,3-difluoro-phenyl)-acrylonitrile |
| 2 | 2-fluorophenyl | phenyl | 5-difluoromethoxy-3-trifluoromethyl-pyrazol-1-yl | B | 3-[4-(5-Difluoromethoxy-3-trifluoromethyl-pyrazol-1-yl)-phenyl]-2-(2-fluoro-phenyl)-acrylonitrile |

THE TABLE-continued

| Cpd. No. | R¹ / R² | Cy¹—(R³)ₙ | Y | IC$_{50}$ (μM) | Chemical Name |
|---|---|---|---|---|---|
| 24 | 2,5-difluorophenyl | 1,4-phenylene | pyrazol-1-yl | C | 2-(2,5-Difluoro-phenyl)-3-(4-pyrazol-1-yl-phenyl)-acrylonitrile |
| 49 | 2,5-difluorophenyl | 1,4-phenylene | 3-methyl-pyrazol-1-yl | C | 2-(2,5-difluorophenyl)-3-(4-(3-methyl-1H-pyrazol-1-yl)phenyl)acrylonitrile |
| 42 | 2,5-difluorophenyl | 1,4-phenylene | 3-trifluoromethyl-pyrazol-1-yl | C | 2-(2,5-Difluoro-phenyl)-3-[4-(3-trifluoromethyl-pyrazol-1-yl)-phenyl]-acrylonitrile |
| 8 | 2,3,4-trifluorophenyl | 1,4-phenylene | 3-CF₃, 5-OCF₃-pyrazol-1-yl | B | 3-[4-(3,5-Bis-trifluoromethyl-pyrazol-1-yl)-phenyl]-2-(2,3,4-trifluoro-phenyl)-acrylonitrile |
| 14 | 2,3-difluorophenyl | 1,2-phenylene | 3,5-bis(CF₃)-pyrazol-1-yl | C | 3-[2-(3,5-Bis-trifluoromethyl-pyrazol-1-yl)-phenyl]-2-(2,3-difluoro-phenyl)-acrylonitrile |
| 10 | 3,4,5-trifluorophenyl | 1,4-phenylene | 3,5-bis(CF₃)-pyrazol-1-yl | B | 3-[4-(3,5-Bis-trifluoromethyl-pyrazol-1-yl)-phenyl]-2-(3,4,5-trifluoro-phenyl)-acrylonitrile |
| 9 | 2,3,6-trifluorophenyl | 1,4-phenylene | 3,5-bis(CF₃)-pyrazol-1-yl | A | 3-[4-(3,5-Bis-trifluoromethyl-pyrazol-1-yl)-phenyl]-2-(2,3,6-trifluoro-phenyl)-acrylonitrile |

THE TABLE-continued

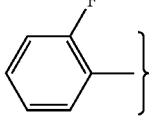

| Cpd. No. | R¹ R² | Cy¹—(R³)ₙ | Y | IC$_{50}$ (μM) | Chemical Name |
|---|---|---|---|---|---|
| 48 | 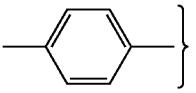 | 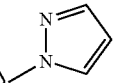 | 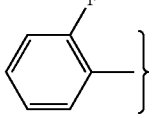 | C | 2-(2-fluoro-phenyl)-3-(4-pyrazol-1-yl-phenyl)-acrylonitrile |
| 6 | 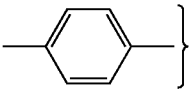 | 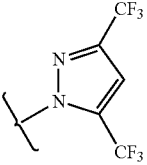 | 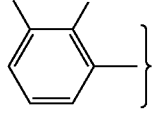 | B | 3-[4-(3,5-Bis-trifluoromethyl-pyrazol-1-yl)-phenyl]-2-(2-fluoro-phenyl)-acrylonitrile |
| 43 | 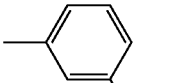 | 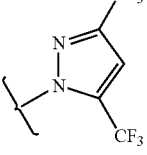 | 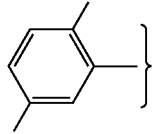 | C | 3-[4-(3,5-Bis-trifluoromethyl-pyrazol-1-yl)-phenyl]-2-(2,3-difluoro-phenyl)-acrylonitrile |
| 44 | 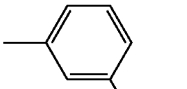 | 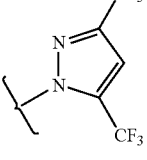 | 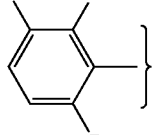 | C | 3-[4-(3,5-Bis-trifluoromethyl-pyrazol-1-yl)-phenyl]-2-(2,5-difluoro-phenyl)-acrylonitrile |
| 11 | 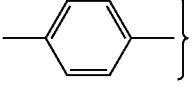 | 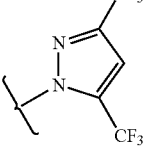 | 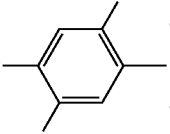 | B | 3-[4-(3,5-Bis-trifluoromethyl-pyrazol-1-yl)-phenyl]-2-(2,3,5-trifluoro-phenyl)-acrylonitrile |
| 12 | 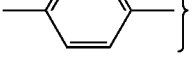 | 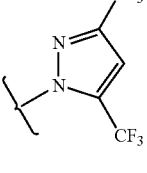 | 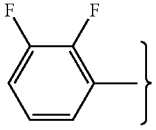 | B | 3-[4-(3,5-Bis-trifluoromethyl-pyrazol-1-yl)-phenyl]-2-(3,4,6-trifluoro-phenyl)-acrylonitrile |
| 45 | 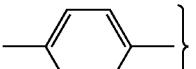 | 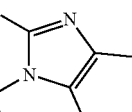 |  | B | 3-(4-(2-(trifluoromethyl)-1H-benzo[d]imidazol-1-yl)phenyl)-2-(2,3-difluorophenyl)acrylonitrile |

THE TABLE-continued

| Cpd. No. | $R^1$ ⟩—<br>$R^2$ | $Cy^1$—$(R^3)_n$ | Y | $IC_{50}$ (μM) | Chemical Name |
|---|---|---|---|---|---|
| 46 | 2,5-difluorophenyl | phenylene | 2-(trifluoromethyl)-1H-benzo[d]imidazol-1-yl | B | 3-(4-(2-(trifluoromethyl)-1H-benzo[d]imidazol-1-yl)phenyl)-2-(2,5-difluorophenyl)acrylonitrile |
| 13 | 2,3-difluorophenyl | 2-chlorophenylene | 3,5-bis(trifluoromethyl)pyrazol-1-yl | C | 3-[4-(3,5-Bis-trifluoromethyl-pyrazol-1-yl)-2-chloro-phenyl]-2-(2,3-difluoro-phenyl)-acrylonitrile |

Note:
The symbol "{" or "}" in the Table indicates the point of attachment of the group.

What is claimed is:

1. A compound represented by the following structural formula:

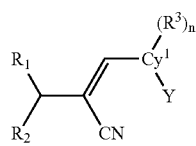

(I)

or a pharmaceutically acceptable salt or solvate thereof wherein:

$Cy^1$ is a monocyclic or bicyclic aromatic or non-aromatic carbocyclyl or heterocyclyl;

Y is an optionally substituted 5-membered heterocyclyl, optionally fused with benzene;

$R^1$ and $R^2$ taken together form a phenyl substituted with one or more lower perfluoroalkoxy or lower perfluoroalkyl;

each $R^3$ is a substituent bonded to $Cy^1$ and is independently selected from halogen, lower alkyl, lower haloalkyl, lower alkoxy, lower haloalkoxy, CN, $NO_2$, $OR^4$, $N(R^4)(R^4)$, $SR^4$, $CO_2R^4$, $CON(R^4)(R^4)$, $SOR^6$, $SO_2R^6$, $COR^4$, $NR^4COR^4$, $NR^4CON(R^4)(R^4)$, $SO_2N(R^4)(R^4)$, $NR^4SOR^6$, and $Ar^2$;

n is an integer selected from 0, 1, 2 or 3;

each $Ar^2$ is independently aryl or heteroaryl optionally substituted with halogen, lower alkyl, lower haloalkyl, lower alkoxy, lower haloalkoxy, CN, $NO_2$, $R^6$, $OR^4$, $N(R^4)(R^4)$, $SR^4$, $CO_2R^4$, $CON(R^4)(R^4)$, $SOR^6$, $SO_2R^6$, $COR^4$, $NR^4COR^4$, $NR^4CON(R^4)(R^4)$, $SO_2N(R^4)(R^4)$, or $NR^4SOR^6$;

each $R^4$ is independently hydrogen or alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio;

each $R^5$ is independently CN or $CO_2R^4$; and each $R^6$ is independently alkyl optionally substituted with one or more amino, alkylamino, alkoxy, alkylthio, oxo (=O), thio (=S), imino (=NH), alkylimino (=N-alkyl), halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, or heterocyclylthio.

2. The compound of claim 1, wherein $Cy^1$ is phenyl.

3. The compound of claim 2, wherein Y is pyrazolyl.

4. A compound represented by the following structural formula:

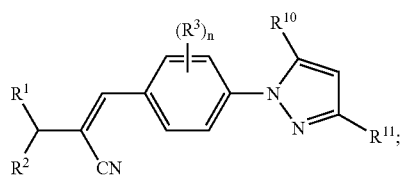

or a pharmaceutically acceptable salt or solvate thereof wherein:

$R^1$ and $R^2$ taken together are phenyl substituted with one or more halogens, lower perfluoroalkyl or lower perfluoroalkoxy;

$R^{10}$ and $R^{11}$ are independently —H, lower alkyl, or lower perfluoroalkyl;

n is an integer selected from 0, 1, 2 or 3; and each $R^3$ is independently —H, lower alkyl, lower haloalkyl, lower alkoxy or lower haloalkoxy.

5. A pharmaceutical composition comprising an effective amount of a compound of claim 1 or a pharmaceutically acceptable salt or solvate thereof and a pharmaceutically acceptable carrier or diluent.

6. A pharmaceutical composition comprising an effective amount of a compound of claim 4 or a pharmaceutically acceptable salt or solvate thereof and a pharmaceutically acceptable carrier or diluent.

* * * * *